(12) United States Patent
Ferreri et al.

(10) Patent No.: US 10,378,055 B2
(45) Date of Patent: Aug. 13, 2019

(54) METHODS AND COMPOSITIONS FOR MEASURING BETA CELL DEATH

(71) Applicant: City of Hope, Duarte, CA (US)

(72) Inventors: Kevin Ferreri, Culver City, CA (US); Mohamed I. Husseiny Elsayed, Torrance, CA (US)

(73) Assignee: City of Hope, Duarte, CA (US)

( * ) Notice: Subject to any disclaimer, the term of this patent is extended or adjusted under 35 U.S.C. 154(b) by 513 days.

(21) Appl. No.: 15/093,359

(22) Filed: Apr. 7, 2016

(65) Prior Publication Data

US 2016/0298193 A1    Oct. 13, 2016

Related U.S. Application Data

(60) Provisional application No. 62/144,816, filed on Apr. 8, 2015.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/154* (2013.01)

(58) Field of Classification Search
CPC ............ C12Q 1/6883; C12Q 2523/125; C12Q 2600/154
See application file for complete search history.

(56) References Cited

U.S. PATENT DOCUMENTS

| 8,211,430 B2* | 7/2012 | Levetan ............. A61K 38/1709 424/133.1 |
| 2014/0256574 A1* | 9/2014 | Herold ................. C12O 1/6883 506/9 |

OTHER PUBLICATIONS

Kuroda et al. Insulin gene expression is regulated by DNA methylation. PLoS One (2009) vol. 4, No. 9, e6953, pp. 1-9.*
Fisher, M.M. et al. (Sep. 2013, e-published Jul. 3, 2013). "Detection of islet β-cell death in vivo by multiplex PCR analysis of differentially methylated DNA," *Endocrinology* 154(9):3476-3481.
Husseiny, M.I. et al. (2012, e-published Oct. 20, 2012). "Development of a quantitative methylation-specific polymerase chain reaction method for monitoring beta cell death in type 1 diabetes," *PloS One* 7(10):e47942.
Husseiny, M.I. et al. (Apr. 10, 2014). "Tissue-specific methylation of human insulin gene and PCR assay for monitoring beta cell death," *PloS One* 9(4):e94591.
Kumaki, Y. et al. (Jul. 1, 2008, e-published May 16, 2008). "QUMA: quantification tool for methylation analysis," *Nucleic Acids Res* 36 (Web Server issue)W170-W175.
Lebastchi, J. et al. (May 2013, e-published Feb. 19, 2013). "Immune therapy and β-cell death in type 1 diabetes," *Diabetes* 62(5):1676-1680.

* cited by examiner

*Primary Examiner* — David C Thomas
(74) *Attorney, Agent, or Firm* — Mintz, Levin, Cohn, Ferris, Glovsky and popeo

(57) ABSTRACT

Provided herein are, inter alia, nucleic acids, methods, and kits for detecting unmethylated DNA in body fluid sample of a subject. The disclosure includes compositions, methods, and kits for detecting unmethylation at a CpG site in an insulin gene promoter of a subject.

32 Claims, 18 Drawing Sheets

Specification includes a Sequence Listing.

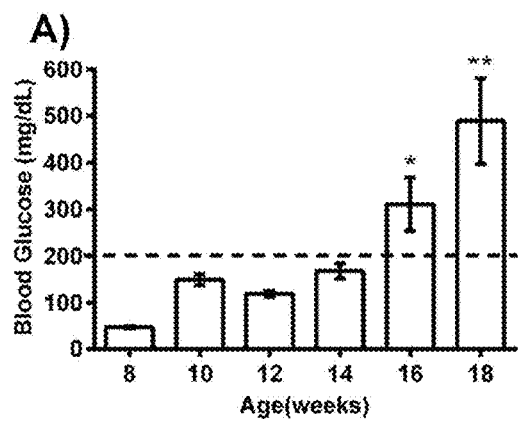
FIG. 1A
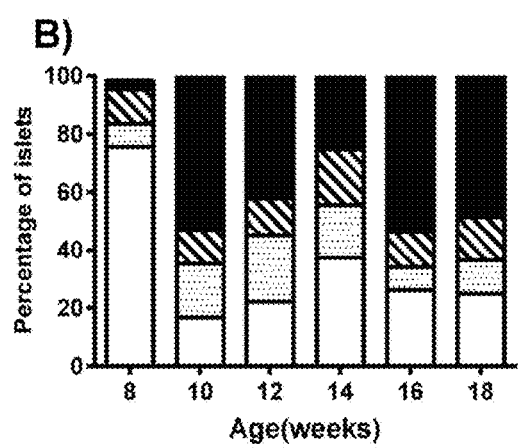
FIG. 1B
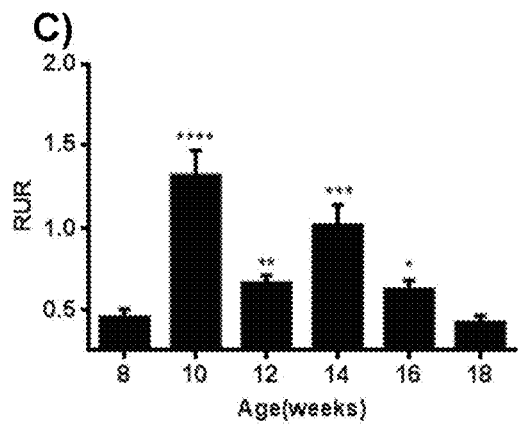
FIG. 1C
FIG. 1

FIG. 4 (Continued)
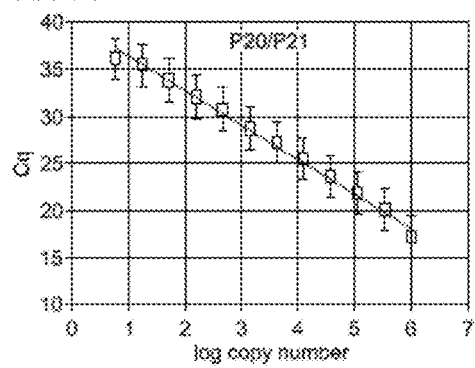
FIG. 4C
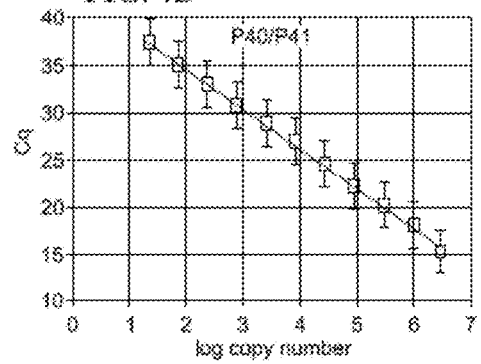
FIG. 4D
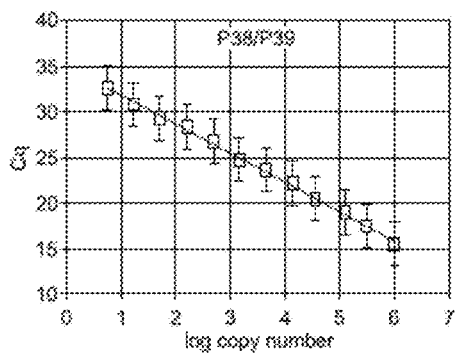
FIG. 4E

FIG. 7 (Continued)
FIG. 7D
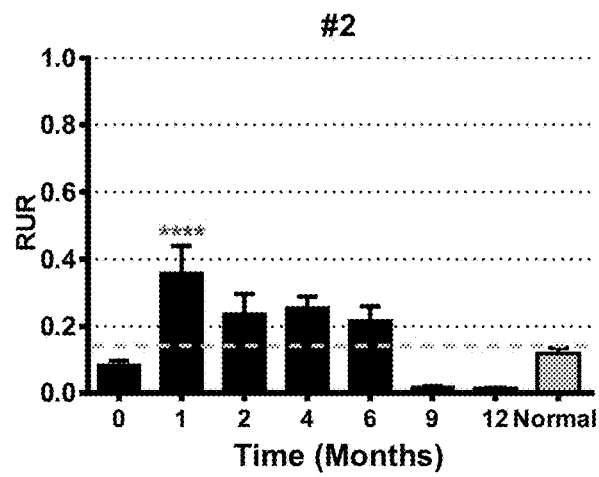
FIG. 7E
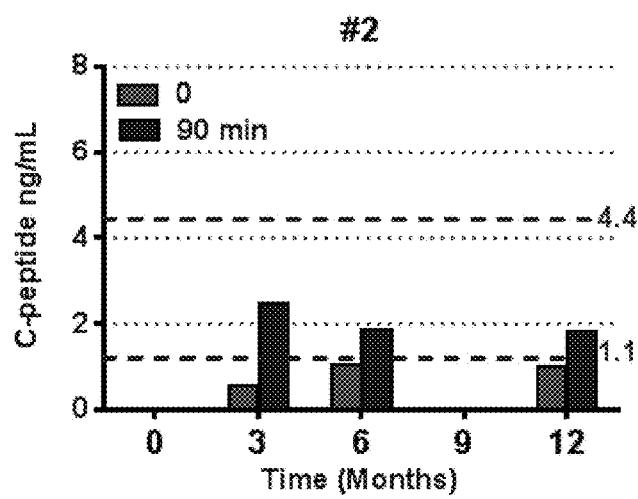
FIG. 7F
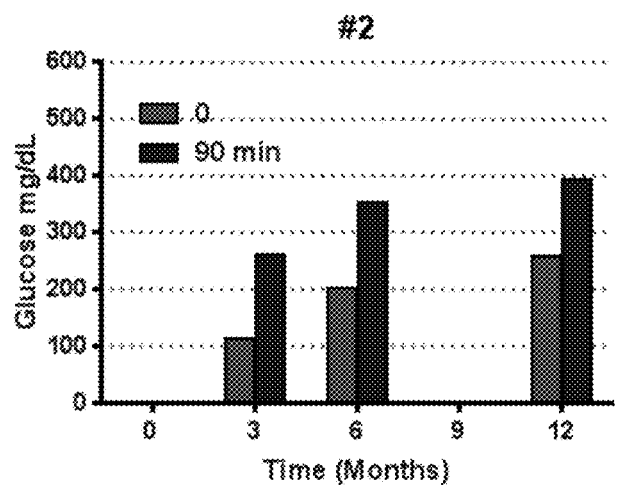

FIG. 7 (Continued)
FIG. 7G
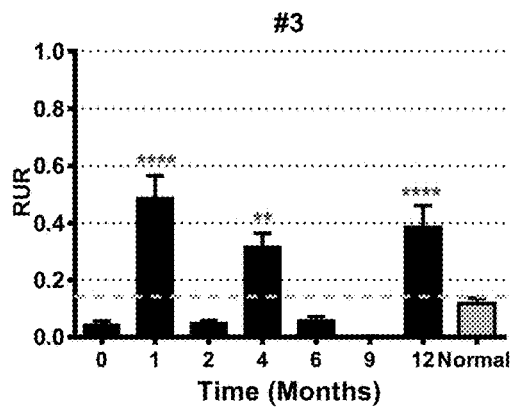
FIG. 7H
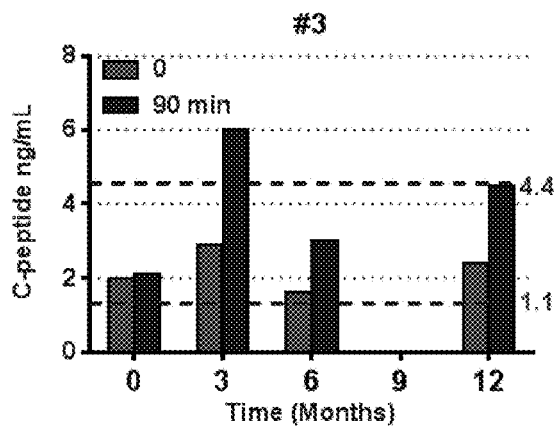
FIG. 7I
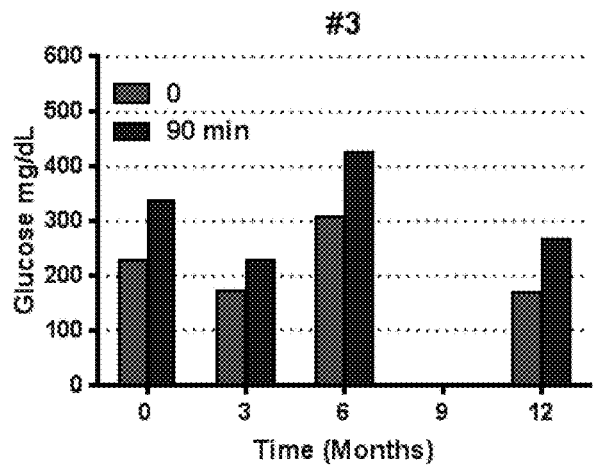

FIG. 7 (Continued)
FIG. 7J
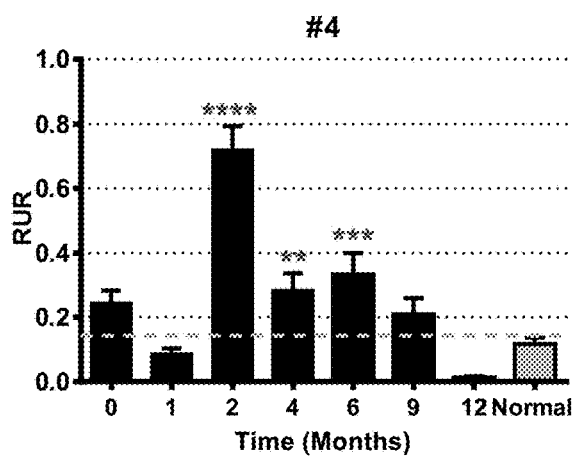
FIG. 7K
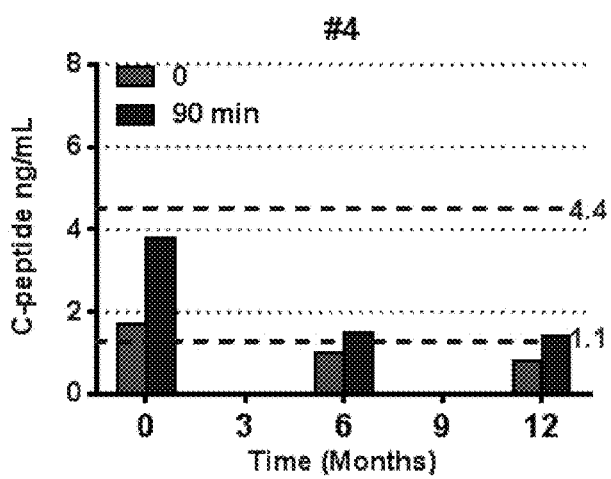
FIG. 7L
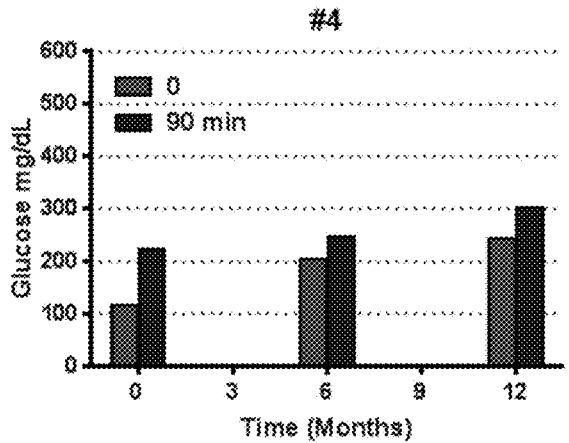

FIG. 7 (Continued)
FIG. 7M
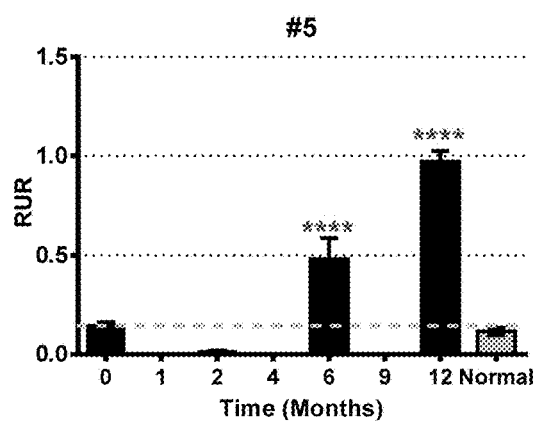
FIG. 7N
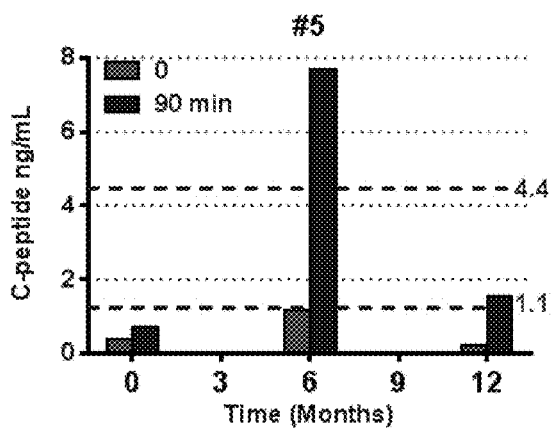
FIG. 7O
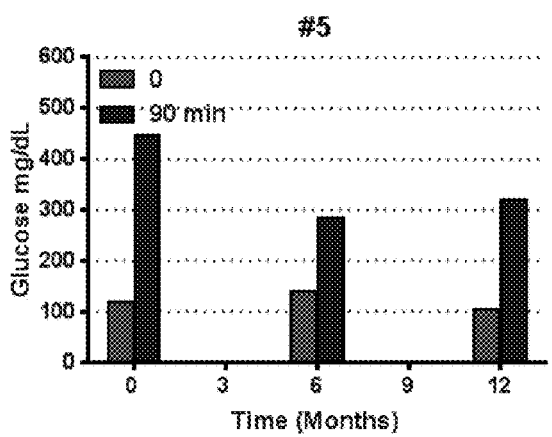

FIG. 7 (Continued)
FIG. 7P
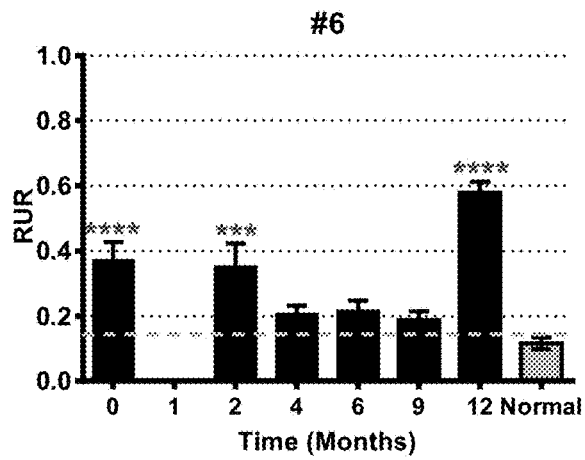
FIG. 7Q
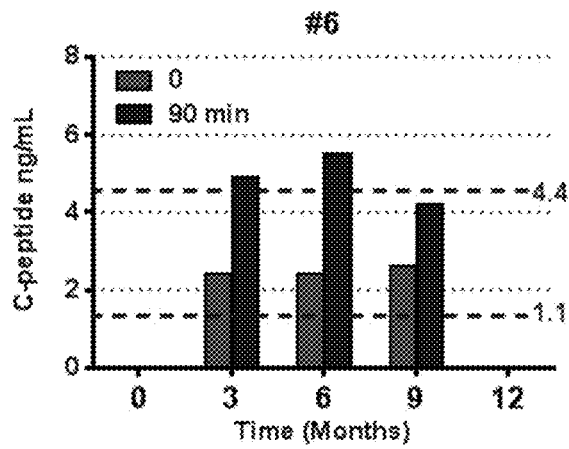
FIG. 7R
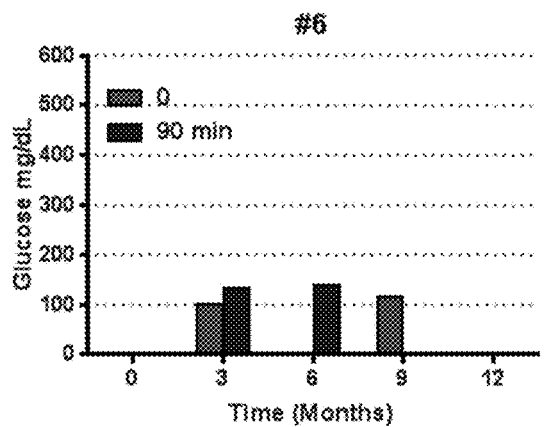

FIG. 7 (Continued)
FIG. 7S
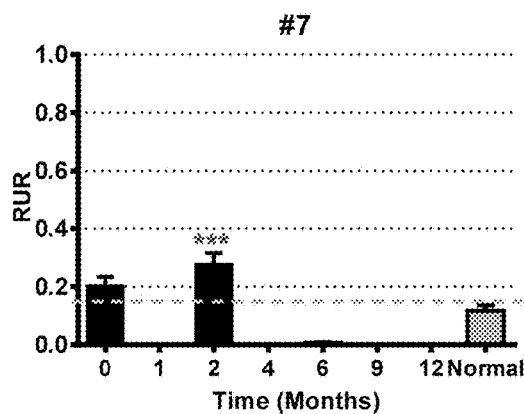
FIG. 7T
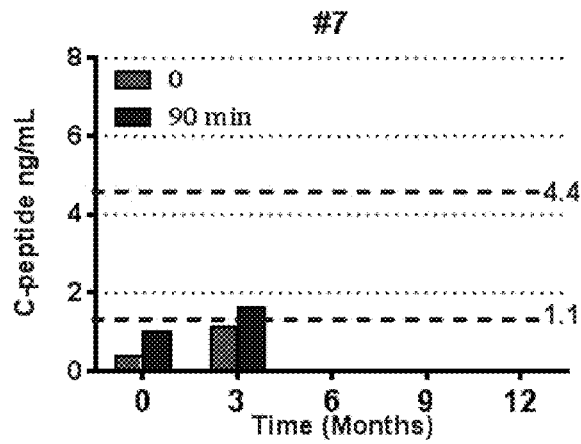
FIG. 7U
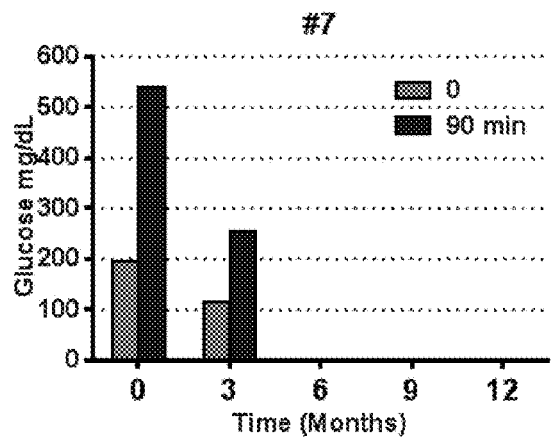

FIG. 7 (Continued)
FIG. 7V
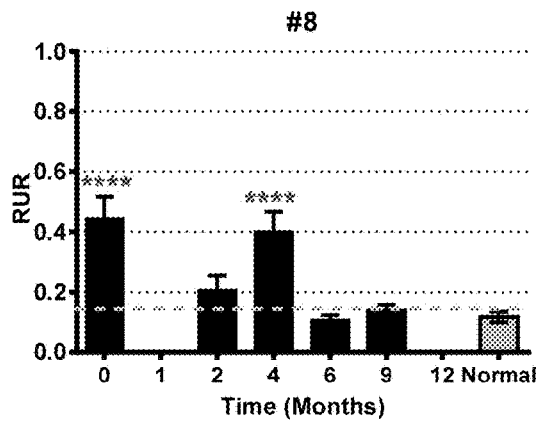
FIG. 7W
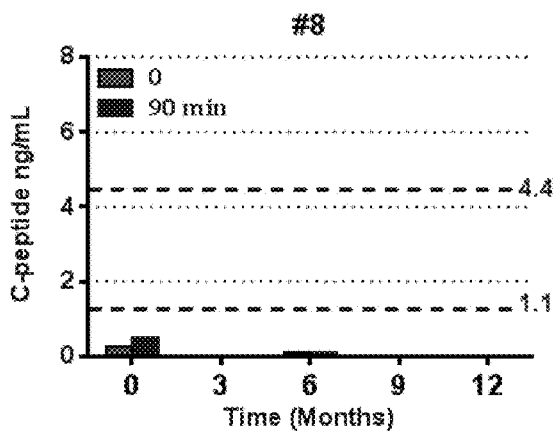
FIG. 7X
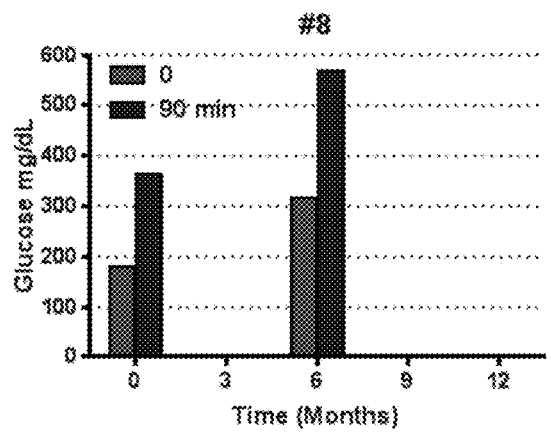

FIG. 7 (Continued)
FIG. 7Y
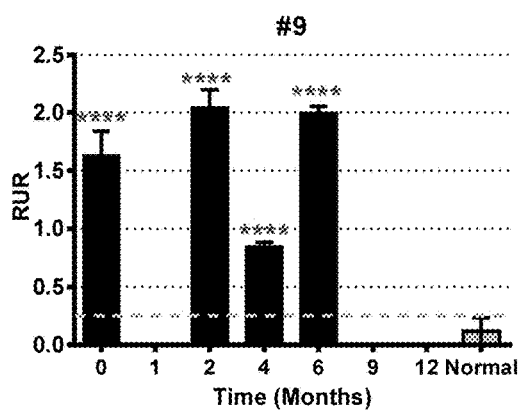
FIG. 7Z
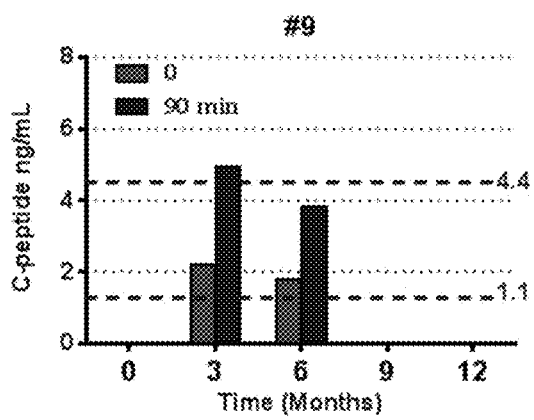
FIG. 7AA
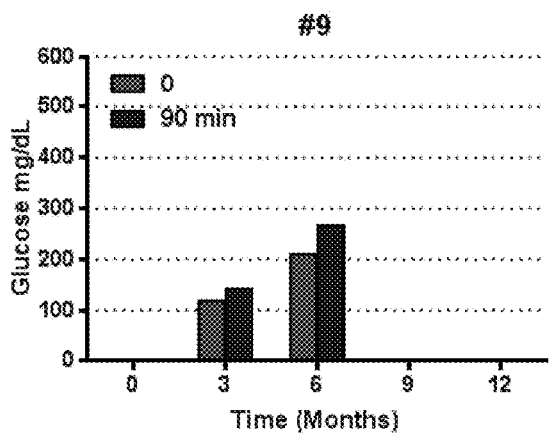

METHODS AND COMPOSITIONS FOR MEASURING BETA CELL DEATH

CROSS-REFERENCES TO RELATED APPLICATIONS

This application claims the benefit of U.S. Provisional Application No. 62/144,816, filed Apr. 8, 2015, which is hereby incorporated in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 48440-567001US_ST25.TXT, created on Apr. 7, 2016, 7,485 bytes, machine format IBM-PC, MS-Windows operating system, is hereby incorporated by reference.

BACKGROUND OF THE DISCLOSURE

Beta cell dysfunction and death is, in part, due to autoimmunity against beta cells, which contributes to the rising blood glucose level in patients with type 1 diabetes (T1D). There is a correlation between autoantibody positivity and loss of beta cell function. However, in order to identify individuals not only at risk but with actual ongoing disease prior to loss of metabolic control, a direct measure of beta cell death is needed. Provided herein are solutions to these and other problems in the art.

BRIEF SUMMARY OF THE DISCLOSURE

The current disclosure provides, inter alia, a quantitative methylation specific nested primer based polymerase chain reaction (qMSP) assay, to identify individuals not only at risk of T1D, but with actual ongoing disease prior to loss of metabolic control. The compositions, methods, and kits provided in this disclosure allow, for example, functional screening of at risk individuals, monitoring of ongoing disease, as well as in evaluating treatment methods including islet cell transplantation. The subject matter provided herein further relates to, inter alia, compositions, methods, and kits detecting unmethylated deoxyribonucleic acid (DNA) in blood of a subject. The disclosure further provides, inter alia, compositions, methods, and kits for detecting unmethylation of isolated DNA from blood of a subject at a CpG site in an insulin gene promoter located at −19 bp, −69 bp, −135 bp, −206 bp, or −357 bp relative to the transcription start site. In embodiments the insulin gene promoter is on DNA from beta cells and isolated from blood of a subject.

The present disclosure provides a method of detecting unmethylated promoter DNA in insulin gene. The method involves modifying DNA isolated from whole blood, plasma, serum, or a tissue sample of a subject to produce a modified DNA. In the method of the present disclosure, DNA is contacted with bisulfite for modifying unmethylated cytosine at a CpG site in the DNA to uridine. The DNA is modified by deamination of cytidine (or nucleoside cytosine) to uridine (or nucleoside uracil). The modified DNA is amplified by using quantitative methylation-specific polymerase chain reaction (qMSP) with methylation specific primers. The method provides detecting unmethylation at a CpG site.

In another aspect, the present disclosure provides nucleotides of SEQ ID NO: 1, 2, 3, and 4. The disclosure further provides nucleic acid comprising SEQ ID NO: 1, 2, 3, or 4, hybridized to a complementary DNA sequence, where the complementary DNA sequence is modified to have uridine.

In a further aspect, kits are provided, in which a first nucleic acid and a second nucleic acid each independently including sequences of SEQ ID NO: 1, 2, 3, 4, 5, or 6, are included. In the kit, the first and second nucleic acids do not simultaneously include the same sequence of SEQ ID NO: 1, 2, 3, 4, 5, or 6. In another aspect, the present disclosure provides a kit including nucleic acids of SEQ ID NO: 1, 2, 3, 4, 5, and 6.

In another aspect, the disclosure provides detecting unmethylated insulin gene promoter in blood of a subject as a measure of beta cell death and a prognostic indicator of autoimmunity resulting in type 1 diabetes (T1D).

In another aspect, the disclosure provides a method for treating an autoimmunity against insulin producing beta cells in a subject having unmethylated CpG at −19 bp, −69 bp, −135 bp, −206 bp, and/or −357 bp relative to the transcription start site of an insulin gene promoter, determined by the method as set forth in this disclosure. In embodiments, the insulin gene promoter is that of DNA from beta cells.

In another aspect, the disclosure provides a system including: at least one processor; and at least one memory including program code which when executed by the one memory provides operations that includes collecting DNA data associated with a subject; contacting said isolated DNA with bisulfite for modifying unmethylated cytosine at a CpG site in said DNA to uridine detecting unmethylation of DNA at said CpG site in an insulin gene promoter located at −19 bp, −69 bp, −135 bp, −206 bp, or −357 bp relative to the transcription start site; and providing, via a user interface, a prognosis and/or diagnosis for the subject based at least in part on detected unmethylated DNA.

Other features and advantages of the invention will be apparent from the following detailed description and claims.

Unless noted to the contrary, all publications, references, patents and/or patent applications reference herein are hereby incorporated by reference in their entirety for all purposes.

BRIEF DESCRIPTION OF THE DRAWINGS

FIGS. 1A-1C show detection of circulating beta cell DNA in non-obese diabetic (NOD) mice using qMSP assay. FIG. 1A depicts bar graphs of blood glucose levels in NOD mice. FIG. 1B depicts a histogram of the degree of insulitis, and FIG. 1C depicts bar graphs of circulating unmethylated beta cell-specific DNA levels. Fold changes in unmethylation were quantified by calculation of the Relative Unmethylation Ration (RUR) for each sample. The data display the mean±standard error mean (SEM) of three independent measurements. The statistical significance was calculated by unpaired t tests compared with week 8 values and indicated by asterisks (*, P<0.05; , P<0.01; * P<0.001, **** P<0.0001).

FIGS. 4A-4E show primer selection and analytical performance of methylation-specific PCR. FIG. 4A depicts a schematic of the human INS gene promoter region, showing the position of nine CpG sites and primer design for quantitative methylation-specific PCR assays. FIG. 4B shows an agarose gel electrophoresis of MSP reactions showing the size of the PCR products. FIG. 4C depicts a graph of real-time PCR data showing linearity of Cq versus log copy number of unmethylated plasmid using P20/P21 primer combination. FIG. 4D depicts a graph of real-time PCR data showing linearity of Cq versus log copy number of unmethylated plasmid using P40/P41 primer combination. FIG. 4E depicts a graph of real-time PCR data showing linearity of Cq versus log copy number of unmethylated plasmid using P38/P39 primer combination.

FIG. 6A depicts bar graph results using blood samples, and FIG. 6B depicts bar graph results using plasma samples. The data display the mean±SEM of the Relative Unmethylation Ratio (RUR) calculations. The statistical significance was calculated with the Wilcoxon test to compare RUR of samples after transplant with that before transplant and significance level indicated by asterisks (*, P<0.05; **, P<0.01).

FIGS. 7A-7C show MSP and MMTT of patient 1; FIGS. 7D-7F show MSP and MMTT of patient 2; FIGS. 7G-7I show MSP and MMTT of patient 3; FIGS. 7J-7L show MSP and MMTT of patient 4; FIGS. 7M-7O show MSP and MMTT of patient 5; FIGS. 7P-7R show MSP and MMTT of patient 6; FIGS. 7S-7U show MSP and MMTT of patient 7; FIGS. 7V-7X show MSP and MMTT of patient 8; and FIGS. 7Y-7AA show MSP and MMTT of patient 9.

DETAILED DESCRIPTION OF THE DISCLOSURE

Figure 2:
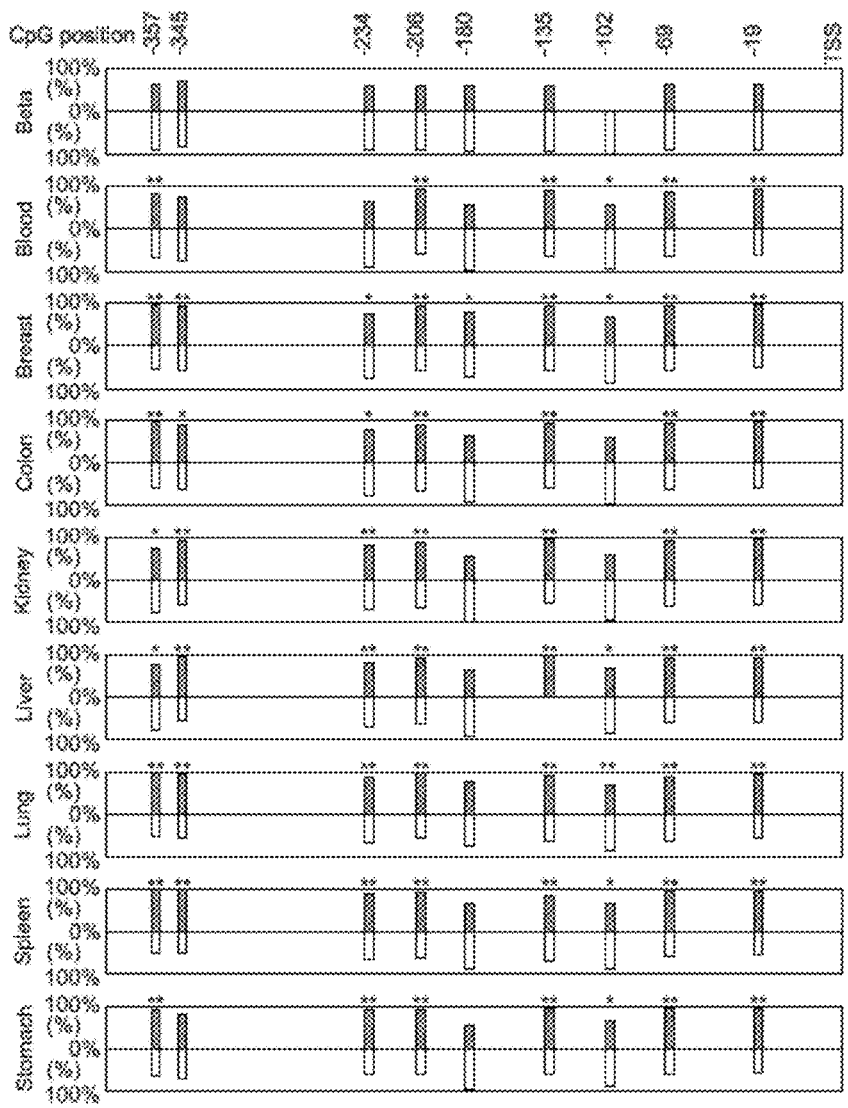
FIG. 2 depicts a histogram of tissue-specific methylation of the human insulin gene (INS) promoter. Statistics were done using the QUMA computer program (Kumaki et al., (2008), *Nucl. Acids Res.*, 36 (suppl. 2): W170-W175) and Fisher exact test comparing each site with the same site in beta cells. The statistical significance is indicated by asterisks (*, P<0.1; **, P<0.01).

Provided herein are, inter alia, compositions, methods, and kits for detecting unmethylated DNA. In some aspects, the present disclosure includes compositions, methods, and kits for detecting unmethylated DNA of insulin gene from beta cells.

The following definitions are included for the purpose of understanding the present subject matter and for constructing the appended patent claims. Abbreviations used herein have their conventional meaning within the chemical and biological arts.

Definitions

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present disclosure, the methods disclosed herein are suitable for use in a patient that is a member of the Vertebrate class, Mammalia, including, without limitation, primates, livestock and domestic pets (e.g., a companion animal). Typically, a patient will be a human patient.

The term "Type 1 Diabetes (T1D)" is used in the usual customary sense, which is a condition in which the immune system destroys insulin-producing cells of the pancreas, thereby compromising or reducing the ability to use glucose (blood sugar) for energy. T1D usually occurs in children and young adults.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes all members of the animal kingdom prone to suffering from the indicated disorder. In some aspects, the subject is a mammal, and in some aspects, the subject is a human.

It must be noted that as used herein and in the appended embodiments, the singular forms "a," "an," and "the" include the plural reference unless the context clearly dictates otherwise. Thus, for example, a reference to "a disease," "a disease state", "a nucleic acid" or "a CpG site" is a reference to one or more such embodiments, and includes equivalents thereof known to those skilled in the art and so forth.

Throughout the description and claims of this specification the word "comprise" and other forms of the word, such as "comprising" and "comprises," means including but not limited to, and is not intended to exclude, for example, other components.

A "control" sample or value refers to a sample that serves as a reference, usually a known reference, for comparison to a test sample. For example, a test sample can be taken from a patient suspected or at risk of having T1D and compared to samples from a known T1D patient, or a known normal (non-disease) individual. A control can also represent an average value gathered from a population of similar individuals, e.g., T1D patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a disease is present in the subject. Similarly, the term "prognosis" refers to a relative probability that a certain future outcome may occur in the subject. For example, in the context of the present disclosure, prognosis can refer to the likelihood that an individual will develop a disease, or the likely severity of the disease (e.g., severity of symptoms, rate of functional decline, survival, etc.). The terms are not intended to be absolute, as will be appreciated by any one of skill in the field of medical diagnostics.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids, including ribonucleic acids (RNA) and deoxyribonucleic acids (DNA), and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "bp" and the like refer, in the usual and customary sense, to the indicated number of base pairs.

The term "promoter" and the like in the usual and customary sense, is a region of DNA that initiates transcription of a particular gene. Promoters are located near the transcription start sites of genes, on the same strand and upstream on the DNA (towards the 5' region of the sense strand). Upstream and downstream in the usual and customary sense both refer to a relative position in DNA or RNA. Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the RNA molecule and downstream is toward the 3' end. When considering double-stranded DNA, upstream is toward the 5' end of the coding strand for the gene in question and downstream is toward the 3' end. Due to the anti-parallel nature of DNA, this means the 3' end of the template strand is upstream of the gene and the 5' end is downstream.

The terms "identical" or percent "identity," in the context of two or more nucleic acids (e.g., genomic sequences or subsequences or coding sequences) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

In some examples of the disclosed methods, when the expression level of a biomarker(s) is assessed, the level is compared with control expression level of the biomarker(s). By control level is meant the expression level of a particular biomarker(s) from a sample or subject lacking a disease (e.g., T1D), at a selected stage of a disease or disease state, or in the absence of a particular variable such as a therapeutic agent. Alternatively, the control level includes a known amount of biomarker. Such a known amount correlates with an average level of subjects lacking a disease, at a selected stage of a disease or disease state, or in the absence of a particular variable such as a therapeutic agent. A control level also includes the expression level of one or more biomarkers from one or more selected samples or subjects as described herein. For example, a control level includes an assessment of the expression level of one or more biomarkers in a sample from a subject that does not have a disease (e.g., T1D), is at a selected stage of progression of a disease (e.g., T1D), or has not received treatment for a disease. Another exemplary control level includes an assessment of the expression level of one or more biomarkers in samples taken from multiple subjects that do not have a disease, are at a selected stage of progression of a disease, or have not received treatment for a disease.

When the control level includes the expression level of one or more biomarkers in a sample or subject in the absence of a therapeutic agent, the control sample or subject is optionally the same sample or subject to be tested before or after treatment with a therapeutic agent or is a selected sample or subject in the absence of the therapeutic agent. Alternatively, a control level is an average expression level calculated from a number of subjects without a particular disease. A control level also includes a known control level or value known in the art.

The term "cell death" includes "apoptosis", "autophagy", "necrosis", "cornification", "mitotic catastrophe", "anoikis", "excitotoxicity", "wallerian degeneration", "paraptosis", "pyroptosis", "pyronecrosis", and "entosis". A detailed review of certain cell death mechanisms is provided, for example, in Kroemer et al., Classification of Cell Death, *Cell Death Differ.*, (2009), 16(1): 3-11.

The term "programmed cell death" and the like refer, in the usual and customary sense, to death of a cell mediated by an intracellular program and carried out in a regulated process which typically confers advantage during the life cycle of the organism. The term "apoptosis" and the like refer, in the usual and customary sense, to a process of programmed cell death characterized by biochemical events that lead to orderly cell changes and eventual cell death. The term "autography" and the like refer, in the usual and customary sense, to the natural destructive mechanism that disassembles unnecessary or dysfunctional cellular components through a regulated process. Accordingly, apoptosis and autophagy are forms of programmed cell death. The term "non-programmed cell death" and the like refer, in the usual and customary sense, to cell death which is not programmed cell death, e.g., necrosis due to external factors such as trauma, infection, and the like.

The term "associated" or "associated with" in the context of a substance (e.g., unmethylated DNA of insulin gene promoter) or substance activity (e.g., unmethylated DNA of insulin gene promoter activity) or substance function (e.g., unmethylated DNA of insulin gene promoter function) associated with a disease does not necessarily mean that the disease is caused by (in whole or in part), or a symptom of the disease is caused by (in whole or in part) the substance or substance activity or function (i.e., unmethylated DNA of insulin gene promoter, unmethylated DNA of insulin gene promoter activity, unmethylated DNA of insulin gene promoter function).

The term "unmethylated DNA" or "demethylated DNA" means DNA that partially or completely lacks a methyl group conjugated to cytosine in a segment of the DNA. In embodiments, an unmethylated DNA or demehtylated DNA partially or completely lacks a methyl group conjugated to cytosine relative to a control DNA. The control DNA may be, for example, may be a DNA derived from a healthy patient or patient population (e.g. a patient that does not have Type I diabetes). Thus, in embodiments, an unmethylated DNA or demehtylated DNA partially or completely lacks a methyl group conjugated to cytosine relative to the methylation pattern observed on an equivalent DNA sequence derived from a patient that does not have Type I diabetes. DNA methylation typically occurs in a CpG dinucleotide context. In the context of the present disclosure, the DNA can be equivalent to a short (2-50 nucleotides, e.g. 5-50 nucleotides) double stranded or single stranded nucleic acid, a nucleic acid fragment cloned in a plasmid DNA, a nucleic acid fragment amplified from a sample of a subject, and/or synthetically prepared a nucleic acid fragment. DNA methylation at the 5' position of cytosine may have the specific effect of reducing gene expression in vivo. DNA methylation may also form the basis of chromatin structure, which typically enables a single cell to grow into multiple organs or perform multiple functions.

The CpG sites or CG sites are regions of DNA where a cytosine nucleotide occurs next to a guanine nucleotide in the linear sequence of bases along its length. "CpG" is shorthand for "—C-phosphate-G-", that is, cytosine and guanine separated by only one phosphate; phosphate links any two nucleosides together in DNA. The "CpG" notation is used to distinguish this linear sequence from the CG base-pairing of cytosine and guanine. The CpG notation can also be interpreted as the cytosine being 5' prime to the guanine base.

In embodiments, Methylation-Specific PCR is based on a chemical reaction of sodium bisulfite with DNA that converts unmethylated cytosines of CpG dinucleotides to uracil or UpG, followed by traditional PCR. However, methylated cytosine is not converted in this process, and primers are designed to overlap the CpG site of interest, which allows one to determine methylation status as methylated or unmethylated.

Relative Unmethylation Ratio (RUR) as used in this disclosure is based on Relative Expression Ratio (RER) described by Husseiny et al. (2012), PloS One 7: e47942.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "administration" or "administering" refer to the act of providing an agent of the current embodiments or pharmaceutical composition including an agent of the current embodiments to the individual in need of treatment.

By "co-administer" it is meant that a composition described herein is administered at the same time, just prior to, or just after the administration of additional therapies. The compound or the composition of the disclosure can be administered alone or can be co-administered to the patient. Co-administration is meant to include simultaneous or sequential administration of the compound individually or in combination (more than one compound or agent). The preparations can also be combined, when desired, with other active substances (e.g. to reduce metabolic degradation).

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

The compositions disclosed herein can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Bioniater Sci. Polym. Ed.* 7:623-645, 1995; as biodegradable and injectable gel formulations (see, e.g., Gao *Phann. Res.* 12:857-863, 1995); or, as microspheres for oral administration (see, e.g., Eyles, *J. Phann. Pharmacol.* 49:669-674, 1997).

As used herein, an "effective amount" or "therapeutically effective amount" is that amount sufficient to affect a desired biological effect, such as beneficial results, including clinical results. As such, an "effective amount" depends upon the context in which it is being applied. An effective amount may vary according to factors known in the art, such as the disease state, age, sex, and weight of the individual being treated. Several divided doses may be administered daily or the dose may be proportionally reduced as indicated by the exigencies of the therapeutic situation. In addition, the compositions/formulations of this disclosure can be administered as frequently as necessary to achieve a therapeutic amount.

As used herein, the term "cytokine" is a term used for proteins released by one cell population which act on another cell as intercellular mediators. Certain examples of such cytokines are lymphokines, monokines, and traditional polypeptide hormones. Included among the cytokines are, e.g., growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor α and β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, β, and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12, IL-13, IL-16, IL-17, IL-18, IL-22, IL-23, IL-27, IL-35, IL-35; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

Pharmaceutical compositions may include compositions wherein the therapeutic drug (e.g., agents described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of therapeutic drug effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and agents of this disclosure. Adjustment and manipulation of established dosages (e.g., frequency and duration) are well within the ability of those skilled in the art.

For any therapeutic agent described herein, the therapeutically effective amount can be initially determined from cell culture assays. Target concentrations will be those concentrations of therapeutic drug(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring agent's effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the therapeutic drug being employed. The dose administered to a patient should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the agent. Thereafter, the dosage is increased by small increments until the optimum effect under circumstances is reached. Dosage amounts and intervals can be adjusted individually to provide levels of the administered agent effective for the particular clinical indication being treated. This will provide a therapeutic regimen that is commensurate with the severity of the individual's disease state.

A weight percent of a component, unless specifically stated to the contrary, is based on the total weight of the formulation or composition in which the component is included.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA) relative to the state in the absence of a compound or composition of the present disclosure.

The terms "phenotype" and "phenotypic" as used herein refer to an organism's observable characteristics such as onset or progression of disease symptoms, biochemical properties, or physiological properties.

The word "expression" or "expressed" as used herein in reference to a DNA nucleic acid sequence (e.g. a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 *Molecular Cloning: A Laboratory Manual*, 18.7-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The term "an amount of" in reference to a polynucleotide or polypeptide, refers to an amount at which a component or element is detected. The amount may be measured against a control, for example, wherein an increased level of a particular polynucleotide or polypeptide in relation to the control, demonstrates enrichment of the polynucleotide or polypeptide. Thus, in embodiments, an increased amount indicates a greater level or efficiency of grafting HSPCs described herein into a host (e.g. mouse). The term refers to quantitative measurement of the enrichment as well as qualitative measurement of an increase or decrease relative to a control.

Throughout the description and claims of this specification the word "comprise" and other forms of the word, such as "comprising" and "comprises," means including but not limited to, and is not intended to exclude, for example, other components.

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "beta cell" the like refer, in the usual and customary sense, to cells found in the pancreatic islets, the primary function of which is storage and release of insulin.

Method of Detecting Unmethylated DNA

Provided herein is a method of detecting unmethylated DNA in a subject. The method includes detecting unmethylation of a DNA sample isolated from a sample of a subject. In some aspects, the sample is a body fluid of a subject. The body fluid may be blood, saliva, and/or tears. In some aspects the blood is whole blood, plasma, or serum. In embodiments, the DNA sample is isolated from a tissue sample, e.g., stomach, spleen, lung, kidney, colon, pancreas, and/or breast, of the subject. The method may also include detecting unmethylation of a control DNA sample. The method may involve isolating DNA from a sample of the subject, and detecting unmethylation of the isolated DNA at a CpG site. The method provides detecting unmethylation at CpG site in the insulin gene of a subject. For example, the method provides detecting unmethylation at a CpG site in the promoter region or an exon of the insulin gene. For example, the method provides detecting unmethylation at a CpG site in the promoter region of the insulin gene. The method may also include detecting unmethylation at a CpG site in an exon and an intron of the insulin gene.

The present disclosure includes a method for detecting unmethylated promoter region of insulin gene, in which insulin DNA is treated with bisulfite to convert unmethylated cytosine to uracil while sparing any methylated cytosine. The amplification of the bisulfite treated DNA with bisulfite-specific primer (BSP) using polymerase chain reaction (PCR) specifically amplifies methylated and unmethylated DNA. The amplified DNA using the BSP primers is then used to perform a second PCR, e.g., methylation sensitive PCR, using two or more different methylation specific primers (MSP) which amplifies a segment containing unmethylated CpG site. The methylation specific primers of the present disclosure match and hybridize to a complementary unmethylated template DNA. In the second-step of the PCR, the products from the first reaction are used as a template for quantitative PCR (qPCR) with nested primers. In embodiments, the present disclosure includes a quantitative MSP (qMSP) method. In embodiments, qMSP of the present disclosure is sensitive and specific for detection of rare DNA. The qMSP may also differentiate between methylated and unmethylated DNA by using oligonucleotide primers whose 3'-ends match the methylation status of specific CpG sites in a bisulfite treated template. In embodiments, two MSP PCRs are performed sequentially with two sets of MSPs, in which a first MSP PCR using one set of nested methylation specific primers is followed by a second MSP PCR using a second set of nested methylation specific primers, which detects CpG sites at the insulin gene promoter. For example, the method may detect unmethylation at CpG site located at −19 bp, −69 bp, −135 bp, −206 bp, or −357 bp of the insulin gene (see Husseiny M I et al., *Tissue-specific methylation of human insulin gene and PCR assay for monitoring beta cell death*, PLoS One. 2014 Apr. 10; 9(4):e94591), or sites equivalent thereto. In embodiments, the insulin gene is the human insulin gene. For example, the insulin gene is of pancreatic cells of a human subject. For example, the insulin gene is of the islets of Langerhans of a human subject. For example, the insulin gene is of beta cells (β cells) of the islets of Langerhans in the pancreas of a human subject.

In embodiments, the beta cells of a human subject are undergoing cell death. For example, non-limiting examples of cell death is due to "apoptosis", "autophagy", "necrosis", "cornification", "mitotic catastrophe", "anoikis", "excitotoxicity", "wallerian degeneration", "paraptosis", "pyroptosis", "pyronecrosis", and "entosis". In embodiments, the beta cells in a human subject are dying due to an autoimmune response. For example, an autoimmune response of a human subject destroys or causes death of the beta cells.

The present disclosure includes a method of detecting unmethylated DNA in which DNA isolated from whole blood, plasma, serum, or a tissue sample of a subject is modified to produce a modified DNA. In the method of the present disclosure, DNA is modified by deamination of cytidine (or nucleoside cytosine) to uridine (or nucleoside uracil). The modified DNA may include uridine. The modified DNA is amplified by using quantitative methylation-specific polymerase chain reaction (qMSP) with methylation specific primers. The unmethylation is detected at the CpG site.

The method of the present disclosure may include obtaining a blood sample from the subject. The DNA is isolated from the blood samples. The DNA is modified with bisulfite. The DNA is amplified with bisulfite specific primers. Quantitative methylation-specific polymerase chain reaction (qMSP) of the insulin gene promoter is performed with methylation specific primers that bind to complementary sequences on the amplified bisulfite modified DNA. In embodiments, the unmethylation is detected at a CpG site at −19 bp, −69 bp, −135 bp, −206 bp, and/or −357 bp in the insulin gene promoter, or sites equivalent thereto. The blood sample can be whole blood, plasma, or serum.

In embodiments, the insulin gene promoter is the underlined sequence end of SEQ ID NO: 13 or a fragment thereof, a nucleotide sequence of SEQ ID NO: 14, or a homolog thereof. In embodiments the CpG site at −19 bp, for example, is a CG sequence with the "C" (i.e., cytosine) located 19 base pair upstream (i.e, 5') of the transcription start site of SEQ ID NO: 13 (italicized "AGC" sequence). In embodiments, the CpG site at −19 bp, for example, would be an equivalent position upstream of the transcription start site of a homologous insulin promoter. For example, the CpG sites at −19 bp, −69 bp, −135 bp, −206 bp, and −357 bp at SEQ ID NO: 13 are bolded and italicized. In embodiments, CpG sites are located at equivalent positions on a homologous insulin gene promoter.

Human INS Gene

[SEQ ID NO: 13]
GGGGACAGGGGTGTGGGGACAGGGGTGTGGGGACAGGGGTGTGGGGACAG
GGGTCTGGGGACAGGGGTGTGGGGACAGGGGTCCTGGGGACAGGGGTGTG
GGGATAGGGGTGTGGGGACAGGGGTGTGGGGACAGGGGTGTGGGGACAGG
GGTCTGGGGACAGCAG CAAAGAGCCC CCCTGCAGCCTCCAGCT
CTCCTGGTCTAATGTGGAAAGTGGCCCAGGTGAGGGCTTTGCTCTCCTGG
AGACATTTGCCCCCAGCTGTGAGCAGGGACAGGTCTGGCCAC GGCC
CCTGGTTAAGACTCTAATGACC CTGGTCCTGAGGAAGAGGTGCTGA
ACCAAGGAGATCTTCCCACAGACCCAGCACCAGGGAAATGGTC
GAAATTGCAGCCTCAGCCCCCAGCCATCTGC ACCCCCCCACCCCAGG
CCCTAATGGGCCAGG GCAGGGGTTGAGAGGTAGGGGAGATGGGCTCT
GAGACTATAAAGCCAG GGGGCCCAGCAGCCCTC AGCCCTCCAGGACA
GGCTGCATCAGAAGAGGCCATCAAGCAGGTCTGTTCCAAGGGCCTTTGCGT
CAGGTGGGCTCAGGATTCCAGGGTGGCTGGACCCCAGGCCCCAGCTCTGCA
GCAGGGAGGACGTGGCTGGGCTCGTGAAGCATGTGGGGGTGAGCCCAGGGG
CCCCAAGGCAGGGCACCTGGCCTTCAGCCTGCCTCAGCCCTGCCTGTCTCC
CAGATCACTGTCCTTCTGCCATGGCCCTGTGGATGCGCCTCCTGCCCCTGC
TGGCGCTGCTGGCCCTCTGGGACCTGACCCAGCCGCAGCCTTTGTGAACC
AACACCTGTGCGGCTCACACCTGGTGGAAGCTCTCTACCTAGTGTGCGGGG
AACGAGGCTTCTTCTACACACCCAAGACCCGCCGGGAGGCAGAGGACCTGC
AGGGTGAGCCAACTGCCCATTGCTGCCCCTGGCCGCCCCCAGCCACCCCCT
GCTCCTGGCGCTCCCACCCAGCATGGGCAGAAGGGGCAGGAGGCTGCCAC
CCAGCAGGGGGTCAGGTGCACTTTTTTAAAAAGAAGTTCTCTTGGTCACGT
CCTAAAAGTGACCAGCTCCCTGTGGCCCAGTCAGAATCTCAGCCTGAGGAC
GGTGTTGGCTTCGGCAGCCCCGAGATACATCAGAGGGTGGGCACGCTCCTC
CCTCCACTCGCCCCTCAAACAAATGCCCCGCAGCCCATTTCTCCACCCTC
ATTTGATGACCGCAGATTCAAGTGTTTTGTTAAGTAAAGTCCTGGGTGAC
CTGGGGTCACAGGGTGCCCCACGCTGCCTGCCTCTGGGCGAACACCCCAT
CACGCCCGGAGGAGGGCGTGGCTGCCTGCCTGAGTGGGCCAGACCCCTGT
CGCCAGGCCTCACGGCAGCTCCATAGTCAGGAGATGGGGAAGATGCTGGG
GACAGGCCCTGGGGAGAAGTACTGGGATCACCTGTTCAGGCTCCCACTGT
GACGCTGCCCCGGGGCGGGGAAGGAGGTGGGACATGTGGGCGTTGGGGC
CTGTAGGTCCACACCCAGTGTGGGTGACCCTCCCTCTAACCTGGGTCCAG
CCCGGCTGGAGATGGGTGGGAGTGCGACCTAGGGCTGGCGGGCAGGCGGG
CACTGTGTCTCCCTGACTGTGTCCTCCTGTGTCCCTCTGCCTCGCCGCTG
TTCCGGAACCTGCTCTGCGCGGCACGTCCTGGCAGTGGGGCAGGTGGAGC
TGGGCGGGGGCCCTGGTGCAGGCAGCCTGCAGCCCTTGGCCCTGGAGGGG
TCCCTGCAGAAGCGTGGCATTGTGGAACAATGCTGTACCAGCATCTGCTC
CCTCTACCAGCTGGAGAACTACTGCAACTAGACGCAGCCCGCAGGCAGCC
CCACACCCGCCGCCTCCTGCACCGAGAGAGATGGAATAAAGCCCTTGAAC
CAGCCCTGCT.

Human INS promoter: In embodiments, the insulin gene promoter is SEQ ID NO: 14 or a fragment thereof. In embodiments, the CpG sites at −19 bp, −69 bp, −135 bp, −206 bp, and −357 bp at SEQ ID NO: 14 are bolded and italicized, which are positions upstream (i.e., 5') of the transcription start site (SEQ ID NO: 14 does not include the transcription start site). In embodiments, CpG sites are located at equivalent positions on a homologous insulin gene promoter.

[SEQ ID NO: 14]
GACAGGGGTGTGGGGATAGGGGTGTGGGGACAGGGGTGTGGGGACAGGGG
TGTGGGGACAGGGGTCTGGGGACAGCAG CAAAGAGCCC CCCTG
CAGCCTCCAGCTCTCCTGGTCTAATGTGGAAAGTGGCCCAGGTGAGGGCT
TTGCTCTCCTGGAGACATTTGCCCCCAGCTGTGAGCAGGGACAGGTCTGG
CCAC GGCCCCTGGTTAAGACTCTAATGACC CTGGTCCTGAGGA
AGAGGTGCTGA ACCAAGGAGATCTTCCCACAGACCCAGCACCAGGGA
AATGGTC GAAATTGCAGCCTCAGCCCCCAGCCATCTGC ACCCC
CCCACCCCAGGCCCTAATGGGCCAGG GCAGGGGTTGAGAGGTAGGGG
AGATGGGCTCTGAGACTATAAAGCCAG GGGGCCCAGCAGCCCTC.

Bisulfite converted DNA of Unmethylated CG of Human INS promoter: In embodiments, the bisulfite modified DNA of unmethylated CG sequence of the human INS promoter includes "TG" sequences located at −19 bp, −69 bp, −135 bp, −206 bp, and −357 bp at SEQ ID NO: 15 are bolded and underlined, which are positions upstream (i.e., 5') of the transcription start site (SEQ ID NO: 15 does not include the transcription start site). In embodiments, the bisulfite modified DNA of unmethylated INS promoter with "TG" sequences located at −19 bp, −69 bp, −135 bp, −206 bp, and −357 bp at SEQ ID NO: 15 or equivalents thereof in a homologue is from an INS promoter from beta cells. In embodiments, bisulfite modified sites are located at equivalent positions on a homologous insulin gene promoter.

[SEQ ID NO: 15]
GTGGGGATAGGGGTGTGGGGATAGGGGTGTGGGGATAGGGGTGTGGGGAT
AGGGGTTTGGGGATAGTAGTGTAAAGAGTTTTTGTTTTGTAGTTTTTAGTT
TTTTTGTTTAATGTGGAAAGTGGTTTAGGTGAGGGTTTTGTTTTTTTGG
AGATATTTGTTTTTAGTTGTGAGTAGGGATAGGTTTGGTTATTGGGTTTT
TGGTTAAGATTTTAATGATTTTGTTGGTTTTGAGGAAGAGGTGTTGATGAT
TAAGGAGATTTTTTTATAGATTTAGTATTAGGGAAATGGTTTTGGAAATTG
TAGTTTTAGTTTTTAGTTATTTGTTGATTTTTTTATTTTAGGTTTTAATG
GGTTAGGTGGTAGGGGTTGAGAGGTAGGGGAGATGGGTTTTGAGATTATA
AAGTTAGTGGGGGTTTAGTAGTTTTT.

Bisulfite converted DNA of Methylated CG of Human INS promoter: In embodiments, the bisulfite modified DNA of methylated CG sequence of the human INS promoter includes "CG" sequences located at −19 bp, −69 bp, −135 bp, −206 bp, and −357 bp at SEQ ID NO: 16 are bolded and underlined, which are positions upstream (i.e., 5') of the transcription start site (SEQ ID NO: 16 does not include the transcription start site). In embodiments, bisulfite modified sites are located at equivalent positions on a homologous insulin gene promoter. In embodiments, the bisulfite modified DNA of methylated INS promoter with "CG" sequences located at −19 bp, −69 bp, −135 bp, −206 bp, and −357 bp at SEQ ID NO: 16 or equivalents thereof in a homologue is from an INS promoter, which is either not from beta cells or a control promoter. In embodiments, the control promoter is from a subject not at risk of or suffering from autoimmunity against beta cells.

[SEQ ID NO: 16]
GTGGGGATAGGGGTGTGGGGATAGGGGTGTGGGGATAGGGGTGTGGGGAT

AGGGGTTTGGGGATAGTAG<u>CG</u>TAAAGAGTTT<u>CG</u>TTTTGTAGTTTTTAGTT

TTTTTGGTTTAATGTGGAAAGTGGTTTAGGTGAGGGTTTTGTTTTTTTGG

AGATATTTGTTTTTAGTTGTGAGTAGGGATAGGTTTGGTTAT<u>CG</u>GGTTTT

TGGTTAAGATTTTAATGATT<u>CG</u>TTGGTTTTGAGGAAGAGGTGTTGA<u>CG</u>AT

TAAGGAGATTTTTTTATAGATTTAGTATTAGGGAAATGGTT<u>CG</u>GAAATTG

TAGTTTTAGTTTTTAGTTATTTGT<u>CG</u>ATTTTTTTATTTTAGGTTTTAATG

GGTTAGG<u>CG</u>GTAGGGGTTGAGAGGTAGGGGAGATGGGTTTTGAGATTATA

AAGTTAG<u>CG</u>GGGGTTTAGTAGTTTTT.

The method of the present disclosure includes methylation specific primers, which hybridize to a CpG site of the insulin gene. For example, the primer hybridizes to a CpG site in the promoter region of the human insulin gene. The method includes detecting methylation or unmethylation at a CpG site in the promoter region of the human insulin gene using specific primers. The method includes methylation specific primers having a sequence of at least SEQ ID NO: 1, 2, 3, and 4. Each of the methylation specific primers of the method does not simultaneously have a sequence of at least SEQ ID NO: 1, 2, 3, and 4. In some aspects, the method includes a methylation specific primer that has a sequence that is at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identical or homologous to a nucleic acid having a sequence of at least SEQ ID NO: 1, 2, 3, or 4.

In embodiments, the methylation specific primers used in the method of the present disclosure are:

```
P20: H-Pro-Bisulf-For1
                                      (SEQ ID NO: 1)
5'-ATAGGGGTGTGGGGATAGGGGTTTGGGGATAGTAGT-3'

P21: H-Pro-Bisulf-Rev1
                                      (SEQ ID NO: 2)
5'-AACCCATCTCCCCTACCTCTCAACCCCTACCA-3'

P38: H-Pro-BS-For4
                                      (SEQ ID NO: 3)
5'-TGGGTTTTTGGTTAAGATTTTAATGATTT-3'

P39: H-Pro-BS-Rev5
                                      (SEQ ID NO: 4)
5'-CAACAAATAACTAAAAACTAAAACTACAATTTCCA-3'

In embodiments, the bisulfite specific
primers are:
P40: MSP-For1
                                      (SEQ ID NO: 5)
5'-ATAGGGGTGTGGGGATAGGGGTTTGGGGATAGTA-3'

P41: MSP-Rev1
                                      (SEQ ID NO: 6)
5'-CAAAACCCATCTCCCCTACCTCTCAACCCCTAC-3'
```

Figure 4A:
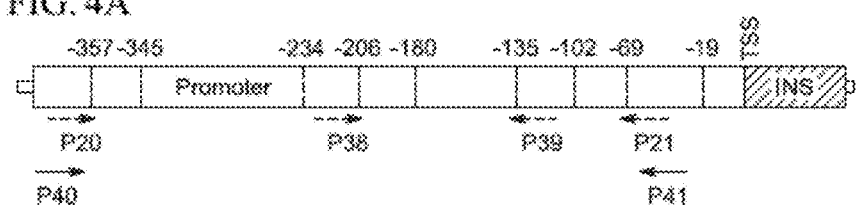
Figure 4B:
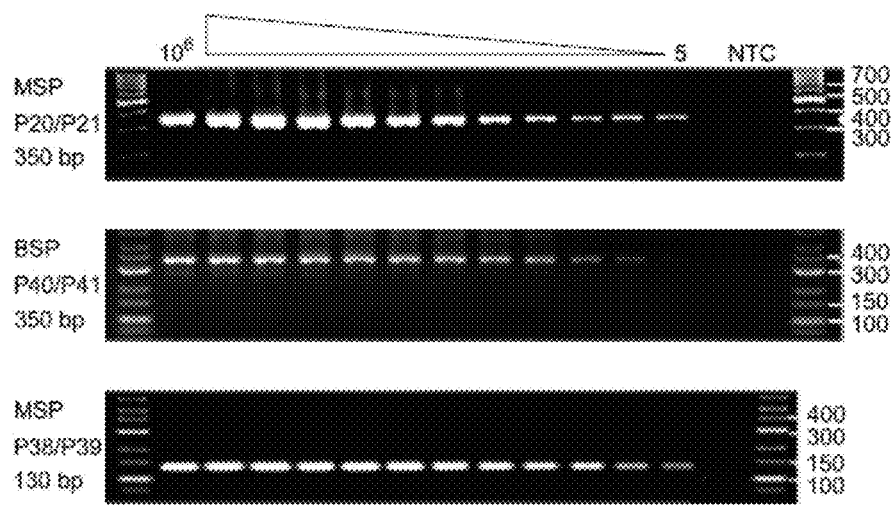

The primers may detect differentially methylated sites (e.g. unmethylated sites) in the promoter region of the human insulin gene. The method includes nested PCR technique that interrogates methylation sites with both high specificity and sensitivity. In embodiments, the primers of the present disclosure are designed to recognize only unmethylated DNA as found in beta cells. Primers P20 (SEQ ID NO: 1) and P21 (SEQ ID NO: 2) are methylation-specific primers (FIG. 4A, dashed arrows) targeting CpGs at −357 bp and −69 bp, respectively, and together produce a product of 350 bp (FIG. 4B). Primers P38 (SEQ ID NO: 3) and P39 (SEQ ID NO: 4) target CpGs −206 bp and −135 bp, respectively, and produce a product of 130 bp (FIG. 4B). Primers P40 (SEQ ID NO: 5) and P41 (SEQ ID NO: 6), target the regions just upstream and downstream of P20 (SEQ ID NO: 1) and P21 (SEQ ID NO: 2), respectively, and do not align with any CpG site (FIG. 4A, solid arrows). P40 (SEQ ID NO: 5) and P41 (SEQ ID NO: 6) are bisulfite-specific (BSP) and amplify a 350 bp product from both methylated and unmethylated DNA, and therefore provide a measure of total amplifiable insulin gene promoter sequences (FIG. 4B). The BSP amplified product is used for detecting specific unmethylation using nested PCR. In embodiments, two nested PCRs are performed sequentially. For example, in some aspects, PCR with P20 (SEQ ID NO: 1)/P21 (SEQ ID NO: 2) is followed by PCR with P38 (SEQ ID NO: 3)/P39 (SEQ ID NO: 4) is performed. In some aspects, the two rounds of nested MSP PCRs using with P20 (SEQ ID NO: 1)/P21 (SEQ ID NO: 2) is followed by PCR with P38 (SEQ ID NO: 3)/P39 (SEQ ID NO: 4) detects CpG sites by detecting unmethylation at −357/−69 bp and −206/−135 bp, respectively.

In embodiments, the method may include serial dilutions of a cloned unmethylated insulin gene as a template to evaluate the disclosed primers. In embodiments, each MSP and BSP primer set of the present disclosure has a dose dependent amplification ranging from $10^6$ copies to as few as 5 copies of the unmethylated sequences (FIG. 4B). The present disclosure includes quantitative analysis of the standard curves, which shows that the BSP and qMSP assays are linear over a $10^5$-fold range of template concentrations (FIG. 4C). Variation across the nested MSP curve ranged from 2.83% to 6.58% (Table 1).

TABLE 1

Statistical variation of qMSP standard curve.

| Log Copy Number | Average $C_q$ | ±SD | % CV |
|---|---|---|---|
| 1.7 | 28.22 | 0.80 | 2.83 |
| 2.2 | 25.79 | 0.92 | 3.57 |
| 2.7 | 24.29 | 0.75 | 3.09 |
| 3.1 | 23.01 | 0.79 | 3.44 |
| 3.6 | 21.35 | 0.68 | 3.21 |
| 4.1 | 20.07 | 0.77 | 3.86 |
| 4.6 | 17.89 | .0.68 | 3.84 |
| 5.0 | 14.58 | 0.83 | 5.68 |
| 5.5 | 14.36 | 0.48 | 3.35 |
| 6.0 | 10.03 | 0.66 | 6.58 |

$C_q$ is the average of n = 5;
SD = standard deviation,
% CV = percent coefficient of variation [(SD/$C_q$ average) × 100].

Figure 5A:
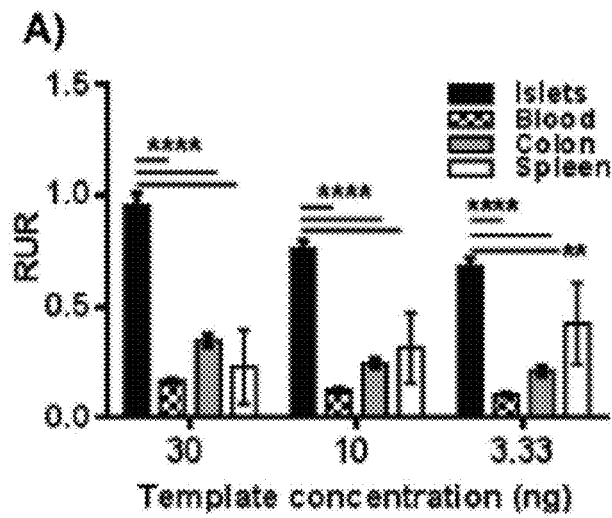
FIGS. 5A-5B show histograms of beta cell specificity of methylation specific primer (MSP) using bisulfate-converted genomic DNA (gDNA) obtained from human islets, blood, and colon used as a template for nested PCR using either bisulfite specific primers (BSP) (FIG. 5A) or MSP (FIG. 5B). The data display the mean±SEM of the Relative Unmethylation Ratio (RUR). The cloned INS promoter was used for normalization and standardization of the results. Statistically significant differences between islets and other tissues were calculated using two-way ANOVA and the significance level indicated by asterisks (P<0.0001).
Figure 5B:
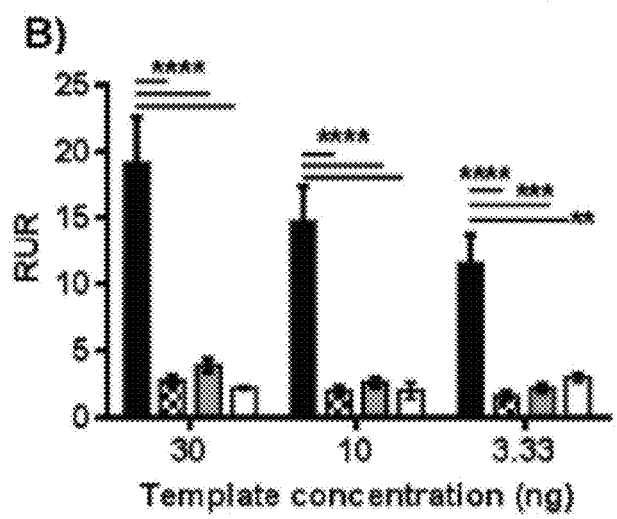

In embodiments, the primers sets may be tested for specificity and sensitivity employing serially diluted bisulfite converted gDNA from human islets, blood, and colon as templates for qMSP. Fold changes in unmethylation may be calculated by the Relative Unmethylation Ratio (RUR) for each sample in which the level of beta cell DNA (qMSP) is normalized for total amplifiable sequences (qBSP). To assess the effect of targeting 2 versus 4 CpG sites, the nested reaction using P38 (SEQ ID NO: 3)/P39 (SEQ ID NO: 4) may be preceded by a first reaction using either BSP primers (P40 (SEQ ID NO: 5)/P41 (SEQ ID NO: 6)) to target a total of 2 sites or MSP primers (P20 (SEQ ID NO: 1)/P21 (SEQ ID NO: 2)) to target 4 sites. The assay interrogating 2 CpG sites was shown to exhibit a highly significant specificity for islets over blood and colon (FIG. 5A). In embodiments, the assay targeting 4 sites shows a greater difference in signal between islets and other tissues, indicating increased specificity of the assay when the number of CpG sites interrogated is increased in the assay (FIG. 5B).

TABLE 2

The amplification efficiency of qMSP and qBSP standard curves.

| PCR type (Primer set) | Efficiency % ± SD | Slope ± SD | $R^2$ ± SD |
| --- | --- | --- | --- |
| Nested MSP (P38/P39) | 85.19 ± 1.37 | −3.737 ± 0.05 | 0.979 ± 0.004 |
| BSP (P40/P41) | 73.44 ± 7.81 | −4.212 ± 0.32 | 0.989 ± 0.01 |

MSP = methylation-specific PCR, BSP = bisulfite-specific PCR, Slope = slope of the standard curve, $R^2$ = the square of the correlation coefficient of the standard curve.

In embodiments, quantitative analysis of standard curves of BSP and qMSP assays are performed. In embodiments, the standard curves are linear over about a $10^5$-fold range of template concentrations (FIG. 4C). Real time PCR may be used to generate labeled PCR products, e.g., SYBR® Green PCR products, to document linearity of Cq versus log copy number of unmethylated plasmid, e.g., from 5 to $10^6$ copies. For nested PCR of the present disclosure, the two MSP assays may be applied sequentially, i.e., amplification with P20/P21 followed by P38/P39. For example, variation across the nested MSP curve of the present disclosure ranged from 2.83% to 6.58% (see Table 1). Furthermore, the standard curve parameters (see Table 2) of the PCR reactions included in the present disclosure are reproducible for both nested qMSP (e.g., efficiency=85.19%±1.37 SD, slope=−3.737±0.05 SD, $R^2$=0.979±0.004 SD; n=5 experiments) and qBSP (e.g., efficiency=73.44%±7.81 SD, slope=−4.212±0.32 SD, $R^2$=0.989±0.01 SD; n=5 experiments).

The method of the present disclosure may be used to detect unmethylation at two or more CpG sites on the insulin gene promoter. In embodiments, the method does not detect unmethylation at a CpG site in the insulin gene promoter located at −102 bp, −180 bp, −234 bp, or −345 bp.

The method of the present disclosure may be used to detect beta cell death by detecting unmethylation at a CpG site at −19 bp, −69 bp, −135 bp, −206 bp, or −357 bp in an human insulin gene promoter, or sites equivalent thereto. In embodiments, beta cell death is not detected by detecting unmethylation at −102 bp, −180 bp, −234 bp, and −345 bp on human insulin gene promoter.

Compositions

Provided herein are compositions of nucleic acids for detecting unmethylated DNA in a subject. In embodiments, the present disclosure includes one or more nucleic acids having a sequence of SEQ ID NO: 1, 2, 3, or 4. In embodiments, each of the nucleic acids is different. Thus, in embodiments, each of the nucleic acids do not simultaneously have the same sequence selected from SEQ ID NO: 1, 2, 3, and 4. In embodiments, the nucleic acid has a sequence that is at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identical or homologous to a nucleic acid having a sequence of at least SEQ ID NO: 1, 2, 3, or 4.

In embodiments, the present disclosure includes a nucleic acid comprising SEQ ID NO: 1, 2, 3, or 4, where the nucleic acid is hybridized to a complementary DNA sequence. In embodiments, the nucleic acid is hybridized to a complementary DNA sequence of the present disclosure. The nucleic acid may have a sequence that is at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identical or homologous to SEQ ID NO: 1, 2, 3, or 4. The complementary sequence can have homology of at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more to a sequence complementary to SEQ ID NO: 1, 2, 3, or 4. The complementary DNA to which the nucleic acid of the present disclosure is hybridized may include a uridine. In embodiments, the present disclosure may include a nucleic acid hybridized to complementary DNA comprising a CpG site.

In embodiments, the present disclosure may further include a DNA comprising a uridine. In embodiments, the DNA may be hybridized to a first nucleic acid and a second nucleic acid each independently comprising SEQ ID NO: 1, 2, 3, or 4. In embodiments, the first and the second nucleic acids are different. In other words, in embodiments, the first and the second nucleic acids do not simultaneously include the same SEQ ID NO: 1, 2, 3, or 4.

In some aspects the first nucleic acid includes SEQ ID NO: 1 and the second nucleic acid includes SEQ ID NO: 2. In embodiments, the first nucleic acid includes SEQ ID NO: 3 and the second nucleic acid includes SEQ ID NO: 4. The DNA may be derived from a biological sample. For example, in embodiments the biological sample is from a human. For example, the biological sample may be whole blood, plasma, or serum of a human.

Kits

Provided herein are kits for detecting unmethylated DNA in a body fluid of a subject. In embodiments, the kits include reagents, such as nucleic acids, for detecting unmethylated DNA from a body fluid, e.g., blood (e.g., whole blood, plasma, and/or serum) of a subject, e.g., human. In embodiments, the present disclosure includes a kit including a first nucleic acid and a second nucleic acid each independently including SEQ ID NO: 1, 2, 3, 4, 5, or 6, in which the first and the second nucleic acids do not simultaneously include the same SEQ ID NO: 1, 2, 3, 4, 5, or 6. In embodiments, the present disclosure includes a kit with a nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NO: 1, 2, 3, or 4.

In embodiments the present disclosure includes a kit containing two nucleic acids, the first nucleic acid including SEQ ID NO: 1 and the second nucleic acid including SEQ ID NO: 2. In embodiments, the present disclosure includes a kit containing two nucleic acids, with a first and a second nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NOs:1 and 2, respectively. In embodiments, a kit of the present disclosure includes two nucleic acids, the first nucleic acid including SEQ ID NO: 3 and a second nucleic acid including SEQ ID NO: 4. In embodiments, the present disclosure includes a kit containing two nucleic acids, with a first and a second nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NOs:3 and 4, respectively. In embodiments, the present disclosure includes a kit containing two nucleic acids, the first nucleic acid including SEQ ID NO: 5 and the second nucleic acid including SEQ ID NO: 6. In embodiments, the present disclosure includes a kit containing two nucleic acids, with a first and a second nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NOs: 5 and 6, respectively.

In embodiments the present disclosure includes a kit containing four nucleic acids, the first nucleic acid including SEQ ID NO: 1, the second nucleic acid including SEQ ID NO: 2, the third nucleic acid including SEQ ID NO:3, and the fourth nucleic acid including SEQ ID NO: 4. In embodiments, the present disclosure includes a kit containing four nucleic acids, with a first, a second, a third, and a fourth nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NOs:1, 2, 3, and 4, respectively.

In embodiments, the present disclosure includes a kit containing six nucleic acids, the first nucleic acid including SEQ ID NO: 1, the second nucleic acid including SEQ ID NO: 2, the third nucleic acid including SEQ ID NO:3, the fourth nucleic acid including SEQ ID NO: 4, the fifth nucleic acid including SEQ ID NO: 5, and the sixth nucleic acid including SEQ ID NO: 6. In embodiments, the present disclosure includes a kit containing six nucleic acids, with a first, a second, a third, a fourth, a fifth, and a sixth nucleic acid that may have a sequence having at least 50%-55%, 55%-60%, 60%-65%, 65%-70%, 70%-75%, 75%-80%, 80%-85%, 90%, 91%, 92%, 93%, 94%, 95%, 96%, 97%, 98%, 99% or more identity or homology to a nucleic acid having a sequence of SEQ ID NOs:1, 2, 3, 4, 5, and 6, respectively.

In embodiments of the present disclosure, the kit(s) may further include enzymes, reagents for deamination of cytosine, buffers, vials, plasmid vectors, control DNA, devices for collecting blood and/or tissue samples, or reagents for labeling DNA, or any combinations thereof. The enzymes are, for example, thermostable DNA polymerase enzymes, restriction enzymes, and combination thereof.

In embodiments, the present disclosure includes a kit including reagents for detecting beta cell death in a subject. The reagents are, e.g., for obtaining blood sample from the subject; isolating DNA from the blood sample; modifying the DNA with bisulfite; amplifying the modified DNA with bisulfite specific primers; performing quantitative methylation-specific polymerase chain reaction (qMSP) of a gene segment, e.g., insulin gene promoter, with methylation specific primers that bind to complementary sequences on the amplified bisulfite modified DNA; and detecting unmethylation at a CpG site at −19 bp, −69 bp, −135 bp, −206 bp, and −357 bp in the insulin gene promoter, or equivalents thereof.

In embodiments, the kit of the present disclosure may include a solid carrier capable of adsorbing the nucleic acids containing in a sample of a body fluid, for example blood (whole blood, plasma, or serum). The kit may also contain other components for example, reagents, in concentrated or final dilution form, chromatographic materials for the separation of the nucleic acids, aqueous solutions (buffers, optionally also in concentrated form for final adjusting by the user) or chromatographic materials for desalting nucleic acids which have been eluted with sodium chloride.

In embodiments, the present disclosure includes a kit in which materials may be included for purifying nucleic acids, for example, inorganic and/or organic carriers and optionally solutions, excipients and/or accessories. Such agents are known and are commercially available. For solid phase nucleic acid isolation methods, many solid supports have been used including membrane filters, magnetic beads, metal oxides, and latex particles.

In addition, in embodiments a kit of the present disclosure can also contain excipients such as, for example, a protease such as proteinase K, or enzymes and other agents for manipulating nucleic acids, e.g., at least one amplification primer, nucleic acid bases (A, T, G, C, and/or U), and enzymes suitable for amplifying nucleic acids, e.g., DNase, a nucleic acid polymerase and/or at least one restriction endonuclease. Alternatively, a commercial polymerase chain reaction kit may be used to amplify the DNA samples.

Method of Detecting Beta Cell Death

Provided herein is a method for detecting circulating beta cell DNA in human islet transplant recipients using qMSP starting at one day post-transplantation and continuing on through several weeks, e.g., two or more weeks. The DNA may be derived from a biological sample. For example, the biological sample may be whole blood, plasma, or serum of a human.

In embodiments, a higher persistent signal of unmethylated insulin promoter DNA in the whole blood compared to the signal from the plasma fraction is achieved. In embodiments of the present disclosure, the presence of blood cells protects the beta cell DNA in circulation. In embodiments of the present disclosure, the qMSP assay to human samples is used to investigate the early stages of human T1D.

In embodiments, the present disclosure includes a method of detecting beta cell death in a human subject in which detecting unmethylation of a CpG site at −19 bp, −69 bp, −135 bp, −206 bp, and/or −357 bp (upstream by location from the transcription start site) of the insulin gene promoter detects beta cell death in the human subject. In embodiments the method may include that CpG sites at −102, −180, −234 and −345 bp of the human insulin gene are unmethylated in stomach, spleen, lung, liver, kidney, colon, breast, blood, and beta cells of the human subject. In embodiments, the present disclosure may include that the detection of unmethylation at a CpG site at −102, −180, −234 and −345 bp does not detect beta cell death and/or early stages of T1D in a subject.

In embodiments, the present disclosure may include a method of detecting eight CpG sites in the exon 2 located at positions +254, +273, +304, +331, +367, +374, +401, and +404 bp; two sites in intron 1 (+127 and +139 bp) and two sites in intron 2 (+456 and +482 bp) relative to the transcription start site of the human insulin gene. In embodiments, the method may include that CpG sites at exon 2 are unmethylated in insulin gene of blood, breast and liver cells. In embodiments, the method may include that detecting unmethylation in the exon 2 is not indicative beta cell death. In embodiments the present disclosure may include that the detection of unmethylation at a CpG site at exon 2 of the insulin gene does not detect beta cell death.

In embodiments the present disclosure may include a method of detecting beta cell death in a human subject at risk of developing type 1 diabetes. In embodiments, the method of the present disclosure includes the qMSP assay, which is used using blood samples, e.g., whole blood, plasma, or serum, from a human subject. In embodiments, the human subject is a clinical islet transplant patient. In embodiments, blood samples, e.g., whole blood, plasma, or serum, from human subjects, e.g., islet transplant recipients are obtained prior to transplantation (TX). In embodiments, samples, e.g., whole blood, plasma, or serum, may be obtained from human subjects on 1 or more days after islet transplant. For example, samples may be obtained after 1 day, 2 days, 3 days, 4 days, 5 days, 6 days, 7 days, 8 days, 9 days, 10 days, 11 days, 12 days, 13 days, 14 days or more after islet transplant.

Type 1 diabetes (T1D) results from the immune-mediated destruction of the insulin-secreting beta cells of the pancreas. The DNA encoding the human insulin gene promoter is uniquely unmethylated in beta cells. In embodiments, the present disclosure includes a methylation-specific PCR (MSP) assay for unmethylated insulin DNA to identify circulating beta cell DNA as a measure of beta cell death. In embodiments, the method disclosed may include a number of patients, e.g., 10 patients with new onset of T1D age 12 years and older starting within the first 3 months of diagnosis, with evaluations throughout their first year post-diagnosis focusing on evidence of beta cell loss as well as glycemic control. In embodiments, all T1D patients of the present disclosure may be diagnosed based on American Diabetes Association (ADA) criteria of elevated blood glucose and, HbA1c, as well as the presence of one or more positive autoantibody titers (such as insulin, GAD65 and IA-2 antibodies). In embodiments, blood samples can be collected at diagnosis, 1, 2, 4, 6, 9, and 12 months post-diagnosis and analyzed by MSP assays. In addition, 90 min stimulated C-peptide level following a mixed-meal tolerance tests (MMTT) may be measured at baseline and quarterly to measure of residual beta cell mass. The longitudinal relationship between these metabolic parameters and the appearance of beta cell DNA in circulation may be analyzed using the MSP assay. In embodiments the present disclosure includes that 60% and 70% of patients may be positive for GAD65 and IA-2 autoantibodies, respectively. In embodiments, HbA1C can range between 9.1% and 18.5% at diagnosis and subsequently decrease after initiation of insulin therapy. In embodiments, stimulated C-peptide levels at diagnosis may be very low but increases with meal stimulation once the patient started insulin therapy, but may decline again over time. In embodiments, the low levels of C-peptide at diagnosis can be a reflection of the toxicity of hyperglycemia to the beta cells and the subsequent improvement with initiation of insulin therapy and control of hyperglycemia probably reflected improvement of beta cell function with glucose control. In embodiments, most of the patients may show a high signal of C-peptide after stimulation but this may be insufficient to control hyperglycemia, indicating that patients still had residual partial beta cells function. Using the MSP assay, in embodiments the present disclosure includes a method by which significantly increased relative unmethylation ratio (RUR) of insulin DNA can be observed, which is compatible with the known timeline of beta cell death in early onset T1D. In embodiments, a decrease in the RUR is observed following the development of diabetes suggesting the arrest of further beta cell death in the pancreas. In embodiments the MSP assay of the present disclosure includes that destruction of beta cells may occur as a result of episodic attacks of autoimmunity in T1D. In embodiments, the present disclosure includes that patients may be in a "honeymoon period" during which the ongoing beta cell death is delayed. In embodiments, the MSP assay of the present disclosure includes an effective method to monitor beta cell destruction in early T1D and is useful in tracking established and innovative measures to ameliorate the disease.

In embodiments, the present disclosure includes methods and compositions to detect tissue-specific methylation pattern in the INS promoter in human beta cells, which distinguishes beta cell DNA from DNA of other tissues. In embodiments, the present disclosure includes that not all methylation of CpG sites in INS promoter of human beta cells are tissue-specific. In embodiments, the present disclosure includes a method by which methylation of the human INS exon 2 is found to be not differentially methylated and, therefore, not suitable for targeting in tissue-specific diagnostics.

Method of Treating Autoimmunity Against Insulin Producing Beta Cells

Provided herein is a method for treating an autoimmunity against insulin producing beta cells in a subject having unmethylated CpG at −19 bp, −69 bp, −135 bp, −206 bp, or −357 bp relative to the transcription start site of an insulin gene promoter, determined by the method as set forth in this disclosure. In embodiments, the subject, e.g., a human subject is diagnosed with autoimmunity against insulin producing beta cells. In embodiments, the subject has type 1 diabetes (T1D). In embodiments, the subject having unmethylated CpG at −19 bp, −69 bp, −135 bp, −206 bp, or −357 bp relative to the transcription start site of an insulin gene promoter is treated for T1D by administering to the subject an active agent for treating T1D, thereby treating T1D of said subject. In embodiments, the active agent insulin. In embodiments, the active agent is rapid-acting insulin or long-acting insulin. In embodiments, the insulin is administered by injection or an insulin pump. In embodiments, the active agent is cyclosporine, anti-CD3 antibody, or anti-CD20 antibody. In embodiments, effective treatments is a combination of agents like anti-CD3 and/or cyclosporine, and further including antigen-specific therapies such as vaccines and/or factors to stimulate beta cell growth. In embodiments, the subject is further treated by transplanting pancreas or islet cells to the subject.

In embodiments, the subject is treated with growth factor and/or cytokine. In embodiments, the subject is treated with one or more of: growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor α and β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, β, and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12, IL-13, IL-16, IL-17, IL-18, IL-22, IL-23, IL-27, IL-35, IL-35; a tumor necrosis factor such as TNF-α or TNF-β; and other polypeptide factors including LIF and kit ligand (KL).

In embodiments, the subject is treated with immunotherapy. For example, in embodiments, the subject is treated with autoantigen-specific regulatory T cell enriched composition. Regulatory T cells (Treg) are a subset of T cells that functionally suppress the proliferation of effector T cell populations which are responsible for pathological responses, both in vitro and in vivo. They are phenotypically characterized as CD4+CD25+ T cells which also express the transcription factor Foxp3. Additionally, they have also been shown to express cell surface markers such as cytotoxic T-lymphocyte antigen-4 (CTLA-4) and glucocorticoid-induced tumor necrosis factor receptor (GITR). CTLA-4 on Tregs can downregulate the co-stimulatory molecules CD80 and CD86 on both murine and human dendritic cells. Tregs can inhibit the co-stimulatory capability of dendritic cells by CD39-mediated inactivation of extracellular ATP, which is an inducer of dendritic cells activation.

Regulatory T cells can become activated and more suppressive. For example, Glycoprotein A repetitions predominant (GARP; also known as leucine-rich repeat protein 32 [LRRC32]) is a marker for activated Tregs that is not found in conventional CD4+ cells. CD44 is enhanced on the surface of activated regulatory T cells and these Tregs then show increased suppressive function. Tregs with a high surface expression of CD101 are more activated and more suppressive.

In embodiments, the method includes modulating an autoimmune reaction in a subject, the method comprising (a) obtaining a population of subject-compatible cells; (b) producing an autoantigen-specific, autoantigen-specific regulatory T cell enriched composition from said population of cells; and (c) introducing the composition into said subject to modulate the autoimmune reaction in the subject. In embodiments, the population of cells is obtained from a subject having unmethylated CpG at −19 bp, −69 bp, −135 bp, −206 bp, or −357 bp relative to the transcription start site of an insulin gene promoter, obtained from a donor distinct from said subject, and/or harvested from peripheral blood of the subjects. The population of cells obtained includes autoantigen-specific regulatory T (Treg) cells, and may be derived from any source in which autoantigen-specific Treg cells exist, such as peripheral blood, the thymus, lymph nodes, spleen, and bone marrow.

In embodiments, the source of Treg cells may be from cadaveric tissue. The population of cells may be obtained from the subject into whom the Treg-enriched composition is subsequently introduced. The subject can be any mammal having unmethylated CpG at −19 bp, −69 bp, −135 bp, −206 bp, or −357 bp relative to the transcription start site of an insulin gene promoter in whom modulation of an autoimmune reaction is desired. Mammals of interest include, but are not limited to: rodents, e.g. mice, rats; livestock, e.g. pigs, horses, cows, etc., pets, e.g. dogs, cats; and primates, e.g. humans. In embodiments, the subject is an animal model of an autoimmune disease. There are numerous, established animal models for using T cell epitopes of autoantigens to induce tolerance, including multiple sclerosis (EAE: experimental autoimmune encephalomyelitis), myasthenia gravis (EMG: experimental myasthenia gravis), neuritis (EAN: experimental autoimmune neuritis), and type 1 diabetes. In an alternate embodiment, the population of cells is obtained from a donor distinct from the subject. The donor is syngeneic, but can also be allogeneic, or even xenogeneic provided the cells obtained are subject-compatible in that they can be introduced into the subject, optionally in conjunction with an immunosuppressive therapy, without resulting in extensive chronic graft versus host disease (GvHD). Allogeneic donor cells are human-leukocyte-antigen (HLA)-compatible, and are typically administered in conjunction with immunosuppressive therapy. To be rendered subject-compatible, xenogenic cells may be subject to gamma irradiation or PEN110 treatment (Fast, L D et al, Transfusion. February 2004; 44(2):282-5). An autoantigen-specific regulatory T (Treg) cell enriched composition is one in which the percentage of autoantigen-specific Treg cells is higher than the percentage of autoantigen-specific Treg cells in the originally obtained population of cells. In embodiments, at least 75%, 85%, 90%, 95%, or 98% of the cells of the composition are autoantigen-specific regulatory T cells.

In embodiments, the composition may further include one or more additional agents, e.g., a costimulatory agent of Treg, a second regulatory T cell stimulatory agent, or agents that generally promote the survival and/or growth of T cells. In embodiments, the costimulatory agent is an antibody or ligand specific for a TCR costimulator, such as CD28 or GITR, as described below. In embodiments, the costimulatory agent is an agonist antibody, such as an agonist antibody which binds to CD28. The stimulatory composition for Treg alternatively includes a second regulatory T cell stimulatory agent. Exemplary stimulatory agents include granulocyte colony stimulating factor, interleukins such as IL-2, IL-6, IL-7, IL-13, and IL-15, and hepatocyte growth factor (HGF). In embodiments, the second stimulating agent is a cytokine, such as an interleukin, such as interleukin-2.

The term "rapid-acting insulin" and the like refer, in the usual and customary sense, to insulin for administration which is formulated to achieve activity in a subject relatively rapidly, e.g., 10, 15, 20 minutes, which peaks in activity relatively rapidly, e.g., 15, 30, 45, 60 minutes. Rapid-acting insulin can continue to provide activity for several hours, e.g., 1, 2, 3, 4, 5, 6 hrs. Exemplary rapid-acting insulin formulation includes insulin glulisine, insulin lispro, and insulin aspart, as known in the art.

The term "long-acting insulin" and the like refer, in the usual and customary sense, to formulations of insulin which reach the bloodstream several hours after administration, e.g., 1, 2, 3, 4 hours or even longer. Long acting insulin tends to regulate (i.e., lower) blood glucose levels fairly evenly over a 24-hr period. Exemplary long-acting insulin preparations include insulin detemir and insulin glargine, as known in the art.

The term "anti-CD3 antibody" and the like refer, in the usual and customary sense, to antibodies directed against a component of the CD3 (i.e, cluster of differentiation 3) T-cell co-receptor, which assembly includes a protein complex composed of four distinct chains in mammals: a CD3γ chain, a CD3δ chain, and two CD3ε chains, as known in the art. Methods for generation of antibodies to CD3 are well known in the art.

The term "anti-CD20 antibody" and the like refer, in the usual and customary sense, to antibodies directed against the B-lymphocyte antigen CD20. CD20 is a glycosylated phosphoprotein expressed on the surface of all B-cells, as known in the art. Methods for generation of antibodies to CD20 are well known in the art.

System for Detecting Unmethylated DNA

Figure 8:
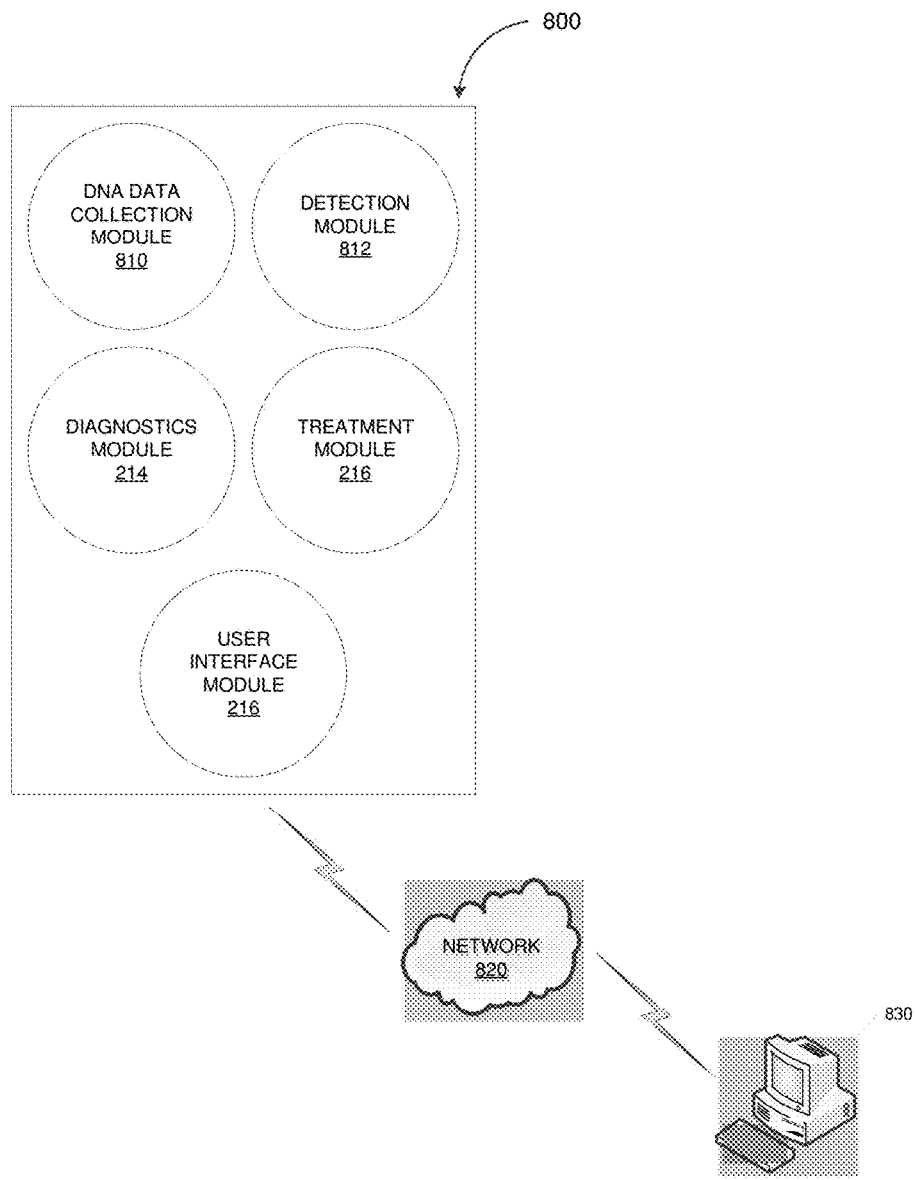
FIG. 8 shows a system diagram illustrating a system for detecting unmethylated DNA in a subject, in accordance with some example embodiments.

Provided herein is a system for detecting unmethylated DNA. FIG. 8 shows a system diagram illustrating a system 800 for detecting unmethylated DNA in a subject, in accordance with some example embodiments. Referring to FIG.

8, in some example embodiments, the system 800 may be realized in digital electronic circuitry, integrated circuitry, specially designed application specific integrated circuits (ASICs), field programmable gate arrays (FPGAs) computer hardware, firmware, software, and/or combinations thereof. The system 800 may be configured to communicate with one or more devices (e.g., personal computers, workstations, tablet personal computers, and/or smartphones) via a wired and/or wireless network 820. For example, as shown, the system 800 may communicate with a device 830.

In some example embodiments, the system 800 may include one or more processor to implement a plurality of modules including, but not limited to, a DNA data collection module 210, a detection module 212, a diagnostic module 214, a treatment module 216, and a user interface module 218. The system 800 may include additional and/or different modules without departing from the scope of the present disclosure.

The DNA data collection module 210 may be configured to collect DNA data. In some example embodiments, the DNA data collection module 210 may collect DNA data that has been generated by isolating DNA from a sample (e.g., fluid, tissue) of a subject. To generate the DNA data, the isolated DNA may be further subject to modification and/or amplification. For example, modifying the isolated DNA may include modifying unmethylated cystosine in the DNA to produce DNA that includes uridine. Thereafter, the DNA including uridine may be amplified through polymerase chain reaction (PCR) (e.g., qMSP) with methylation specific primers.

According to some example embodiments, the DNA data may include sequencing data that corresponds to the amplified DNA. As such, in some embodiments, the DNA data collection module 210 may be communicatively coupled to a DNA sequencer (not shown) adapted to automate the sequencing of DNA that has been isolated, modified, and amplified as discussed above. In addition, in some example embodiments, the DNA data collection module 210 may be communicatively coupled with one or more DNA processing apparatuses (not shown) via the network 820. For example, the DNA data collection module 210 may be coupled with one or more apparatuses adapted to automate the performance DNA isolation (e.g., robotic fluid handling systems), modification, and amplification (e.g., thermal cycler).

The detection module 812 may be configured to detect unmethylated DNA based on DNA data (e.g., collected by the DNA data collection module 810). For example, in some example embodiments, the detection module 812 may be configured to detect unmethylated promoter DNA at a CpG site of the insulin gene. The detection of unmethylated insulin gene promoter may be used as a measure of beta cell death and a prognostic indicator for autoimmunity resulting in T1D.

The diagnostic module 814 may be configured to provide a diagnosis and/or prognosis for a subject based on results from the detection module 812. In example embodiments, based on the unmethylated DNA detected in a subject, the diagnostic module 814 may provide a prognosis of whether the subject is at risk for developing T1D. For example, the diagnostic module 814 may perform statistical analysis (e.g., using QUMA and Fisher exact test) on the detected unmethylated DNA to generate a prognosis for a subject.

Alternatively or additionally, based on the detected unmethylated DNA in the subject, the diagnostic module 814 may also be able to provide a diagnosis of the presence of actual ongoing T1D in the subject. The diagnostic module 814 may be able to provide a diagnosis of the presence of actual ongoing T1D before the subject exhibits any loss of metabolic control.

The treatment module 816 may be configured to devise a treatment plan for a subject based on results from the diagnostic module 814. In some example embodiments, the treatment module 816 may determine, based on a subject's diagnosis and/or prognosis, a treatment plan that includes, but is not limited to, preventative care, medication, and/or islet cell transplantation.

The user interface module 818 may be configured to generate a user interface through which a user (e.g., a physician) may interact with the system 800. For example, the user interface module 818 may provide one or more user interfaces configured to provide a prognosis and/or diagnosis from the diagnostic module 814 and/or a treatment plan from the treatment module 816. The user interfaces may be graphic user interfaces (GUIs) adapted to provide visual outputs to and/or receive inputs from the user.

Figure 9:
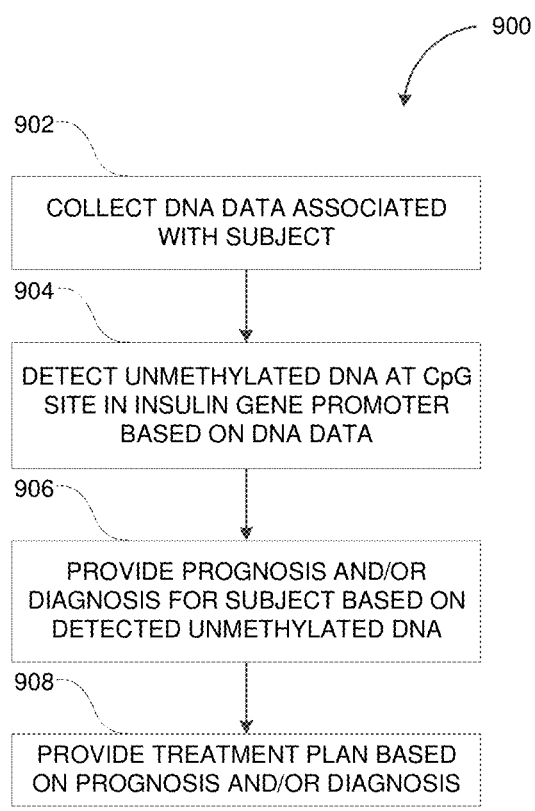
FIG. 9 shows a flowchart illustrating a process for detecting unmethylated DNA in a subject, in accordance with some example embodiments.

FIG. 9 shows a flowchart illustrating a process 900 for detecting unmethylated DNA in a subject, in accordance with some example embodiments. Referring to FIGS. 8-9, the process 900 may be performed by the system 800.

At 902, the system 800 (e.g., the DNA data collection module 810) may collect DNA data associated with a subject. For example, in some example embodiments, the system 800 (e.g., the DNA data collection module 810) may collect DNA data that has been generated by isolating a subject's DNA from a sample (e.g., fluid, tissue). The isolated DNA may have been further modified and/or amplified. According to some example embodiments, the DNA data may be sequencing data (e.g., from a DNA sequencer) that corresponds to the amplified DNA.

At 904, the system 800 (e.g., the detection module 812) may detect unmethylated DNA at a CpG site in an insulin gene promoter based on the DNA data. In some example embodiments, the detection of unmethylated insulin gene promoter may be used as a measure of beta cell death and a prognostic indicator for autoimmunity resulting in T1D.

At 906, the system 800 (e.g., the diagnostic module 814) may provide a prognosis and/or a diagnosis for the subject based on detected unmethylated DNA. In some example embodiments, based on unmethylated DNA detected in a subject, the system 800 may provide a prognosis of the subject's risk for developing T1D and/or a diagnosis of actual ongoing T1D (e.g., before subject exhibits loss of metabolic control).

At 908, the system 800 (e.g., the treatment module 816) may provide a treatment plan based on the prognosis and/or diagnosis. For example, in some example embodiments, the system 800 may determine a treatment plan that includes, but is not limited to preventative care, medication, and/or islet cell transplantation.

The process 900 can include additional and/or different operations without departing from the scope of the present disclosure. One or more operations of the process 900 may be omitted and/or repeated without departing from the scope of the present disclosure.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results.

The following examples are provided as illustrations of various embodiments of the disclosure but are not meant to limit the disclosure in any manner.

EXAMPLES

Example 1: Evaluation of qMSP for Detection of Circulating Beta Cell-Specific DNA in an Autoimmune Mouse Model MSP Detects Beta Cell Death at the Onset of Insulitis in Non-Obese Diabetic (NOD) Autoimmune Mouse Model As part of this study, development of diabetes in the NOD autoimmune mouse model which shares many similarities with type 1 diabetes (T1D) in humans was monitored and assessed by qMSP assays which determine autoimmune-mediate loss of beta cells. The mice (measured every two weeks, n=5) became significantly hyperglycemic (>200 mg glucose/dL) at weeks 16 and 18 ($p=0.01$ and $p=0.004$, respectively) (FIG. 1A). The dashed line in FIG. 1A at 200 mg/dL indicates the hyperglycemic threshold. However, the lymphocyte infiltration of the islets (insulitis) was mildly present even at 8 weeks and showed a significant increase by week 10 and remained high through weeks 12, 14, 16 and 18 ($p=0.0007$, $p=0.01$, $p=0.009$, $p=0.001$, and $p=0.0007$, respectively compared with week 8 (FIG. 1B). As depicted in FIG. 1B, the degree of insulitis scored was no insulitis (white), peri-insulitis (dotted), mild insulitis (hatched) and invasive insulitis (black) for pancreatic sections of the indicated groups (n=5) stained with H&E. Concomitantly, there was a significant rise in circulating unmethylated beta cell-specific DNA starting at week 10 (FIG. 1C) which remained elevated at weeks 12, 14, and 16 ($p<0.0001$, $p=0.0053$, $p=0.0008$, and 0.04, respectively compared with week 8) until it dropped to baseline levels at week 18. In a spontaneous diabetic model, MSP methodology is capable of detecting beta cell death at the onset of insulitis and six weeks prior to the rise in blood sugar.

Example 2: Methylation Pattern of the Human Insulin Gene (INS) Promotor

Isolation of Genomic DNA

Genomic DNA was obtained from human tissues using NucleoSpin Tissue (Clontech, Mountain View, Calif.). In case of plasma obtained from blood of transplant recipient, gDNA was purified using QIAamp MinElute Virus Spin Kit and gDNA obtained from blood of transplant recipient was purified using QIAamp Blood Medi Kit (QIAGEN, Valencia, Calif.).

PCR Cloning of a Fragment from Insulin Gene

Primers H-INS-pro-For and H-INS-exon2-Rev (Table 3) were used to amplify a 900 bp fragment from human gDNA containing the promoter, intron 1, exon 2, and intron 2 of the human insulin gene (INS). The PCR product was cloned into pCR2.1-TOPO plasmid vector (Invitrogen, Carlsbad, Calif.) and used for development of the assay. The cloned sequence was confirmed by the DNA Sequencing/Solexa Core at the Beckman Research Institute of City of Hope using M13F and M13R primers.

Bisulfite Genomic Sequencing

Nucleotide sequence of the human INS (GeneID: 3630) gene was obtained from Genbank and the potential methylation sites (i.e. CG dinucleotides) were identified. Genomic DNA was isolated from various tissues as described above and were treated with EZ DNA methylation-gold kit (Zymo Research, Orange, Calif.) according to the manufacturer's recommendation. The human INS gene was then amplified with pairs of gene-specific primers for promoter and exon 2 (Table 3) in a mixture containing 100 ng bisulfite modified DNA as a template and DNA Hot Star-Taq polymerase (QIAGEN, Valencia, Calif.). Each PCR fragment was TA cloned into pCR2.1-TOPO vector and sequenced as described above. Each pattern resulted from 18-59 clones of INS promoter or 5-33 clones of INS exon 2 obtained from 6 different individuals for blood tissue and 3 individuals from other tissues as indicated in (Table 4). Statistics of each CpG site were done using the QUMA computer program which performs a Fisher exact test.

TABLE 3

Oligonucleotides used in this study.

| | Designation | Sequence |
|---|---|---|
| | \multicolumn{2}{l}{Primers for methylation mapping of human INS promoter} |
| 1 | HINSex2-For | 5'-GGTTTAGGATTTTAGGGTGGTT-3' (SEQ ID NO: 7) |
| 2 | HINSex2-Rev | 5'-CCCCCTTCTACCCATACTAAAT-3' (SEQ ID NO: 8) |
| | \multicolumn{2}{l}{Primers for methylation mapping of human INS exon 2} |
| 1 | HuINS420-For | 5'-TGTGGGGATAGGGGTTTGGGGATAGTA-3' (SEQ ID NO: 9) |
| 2 | HuINS420-Rev | 5'-CCTCTTCTAATACAACCTATCCTAAAAAACT AAAAACTAC-3' (SEQ ID NO: 10) |
| | \multicolumn{2}{l}{Primers for cloning human INS gene} |
| 1 | H-INS-pro-For | 5'-TGTGGGGACAGGGGTCTGGGGACA-3' (SEQ ID NO: 11) |
| 2 | H-INS-exon2-Rev | 5'-AGCCTCCTGCCCCCTTCTGCCCAT-3' (SEQ ID NO: 12) |
| | \multicolumn{2}{l}{Primers for qMSP} |
| P20 | H-Pro-Bisulf-For1 | 5'-ATAGGGGTGTGGGGATAGGGGTTTGGGGATA GTAGT-3' (SEQ ID NO: 1) |
| P21 | H-Pro-Bisulf-Rev1 | 5'-AACCCATCTCCCCTACCTCTCAACCCCTACC A-3' (SEQ ID NO: 2) |
| P38 | H-Pro-BS-For4 | 5'-TGGGTTTTTGGTTAAGATTTTAATGATTT-3' (SEQ ID NO: 3) |
| P39 | H-Pro-BS-Rev5 | 5'-CAACAAATAACTAAAAACTAAAACTACAATT TCCA-3' (SEQ ID NO: 4) |
| | \multicolumn{2}{l}{Primers for qBSP} |
| P40 | MSP-For1 | 5'-ATAGGGGTGTGGGGATAGGGGTTTGGGGATA GTA-3' (SEQ ID NO: 5) |

TABLE 3-continued

Oligonucleotides used in this study.

| | Designation | Sequence |
|---|---|---|
| P41 | MSP-Rev1 | 5'-CAAAACCCATCTCCCCTACCTCTCAACCCCT AC-3' (SEQ ID NO: 6) |

TABLE 4

Mapping of human insulin promoter and exon 2 regions.

| | Promoter | | Exon 2 | |
|---|---|---|---|---|
| Organ tissues | Number of donors tissue | Number of clones | Number of donors tissue | Number of clones |
| Beta cells | 3 | 26 | 2 | 12 |
| Blood | 6 | 59 | 5 | 25 |
| Breast | 3 | 22 | 2 | 5 |
| Colon | 3 | 27 | 3 | 22 |
| Kidney | 3 | 22 | 3 | 14 |
| Liver | 3 | 20 | 3 | 33 |
| Lung | 3 | 24 | 3 | 19 |
| Spleen | 3 | 21 | 3 | 21 |
| Stomach | 3 | 18 | 3 | 13 |

INS promoter in human beta cells exhibited a tissue-specific methylation pattern to distinguish beta cell DNA from DNA of other tissues The promoter of the human INS contains nine potential methylation (CpG dinucleotide) sites that are located at positions −357, −345, −234, −206, −180, −135, −102, −69 and −19 bp relative to the transcription start site (TSS), as indicated in FIG. 2. A broader examination of the tissue-dependent methylation of the human insulin gene was performed.

Genomic DNA from nine different tissues including an enriched beta cell fraction were subjected to bisulfite sequencing of the INS gene to map their respective CpG methylation patterns (FIG. 2). Six different donors for blood and 3 donors for other tissues were used for each sample (human blood, breast, colon, kidney, liver, lung, spleen, stomach and human beta cells 'Islet cell fraction'≈70% islet cells). FIG. 2 displays the position and the percentage of unmethylation (white bars) to methylation (black bars) for each CpG. Analysis of the bisulfite sequencing data revealed that most of the CpG sites in the INS promoter were uniquely unmethylated in pancreatic beta cells but predominantly methylated in other tissues (FIG. 2). Not all of the sites exhibited the same degree of tissue-dependent methylation. The CpGs at −102, −180, −234, and −345 bp were substantially unmethylated in all the tissues examined and were not statistically different from beta cells (FIG. 2). Conversely, sites −19, −69, −135, −206, and −357 bp relative to TSS were unmethylated in beta cells but not in other tissues, and displayed a significant tissue-specificity. Only certain sites in the human INS promoter exhibited a tissue-specific DNA methylation pattern and therefore only these sites can differentiate between beta cells and other tissues.

Example 3: Methylation Pattern of the Human Insulin Gene Exon 2, Intron 1 and Intron 2

Figure 3:
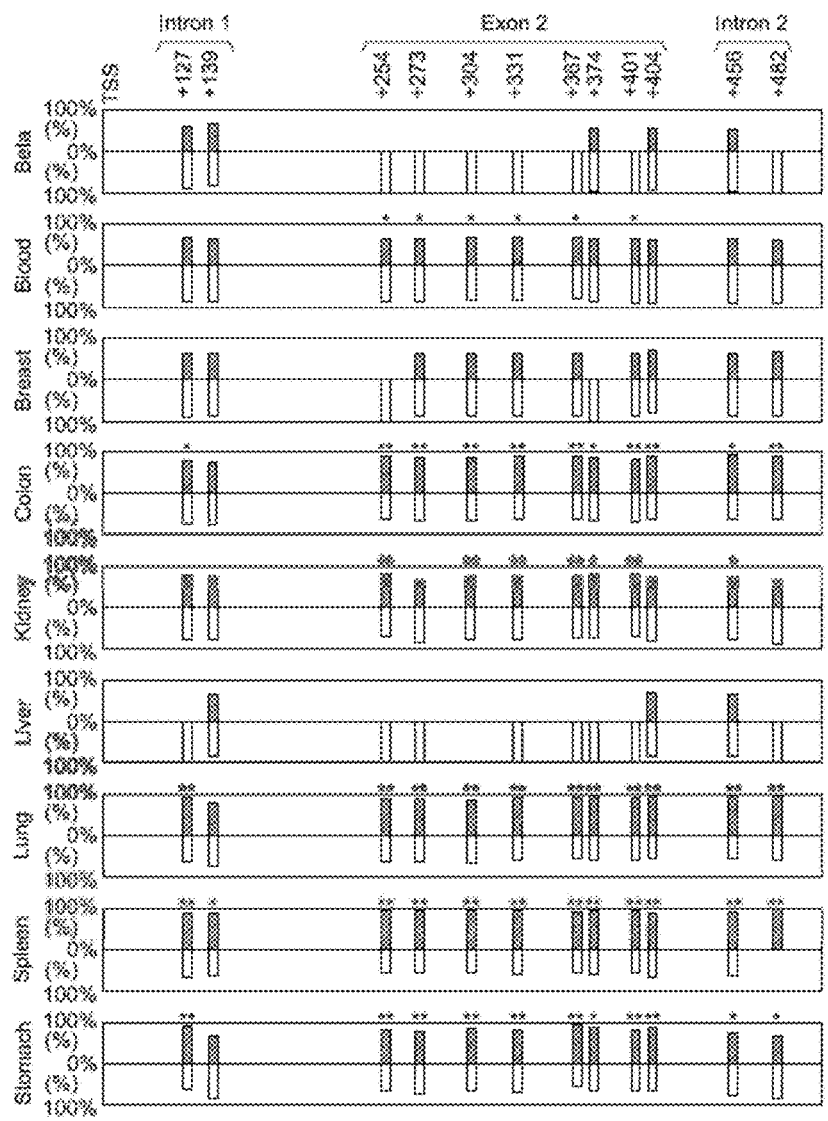
FIG. 3 depicts histogram of tissue methylation pattern of the human INS exon 2 (8CpG), intron 1 (2 CpG) and intron 2 (2 CpG). Statistics were done using the QUMA computer program and Fisher exact test comparing each site with the same site in beta cells. The statistical significance is indicated by asterisks (*, P<0.1; **, P<0.01).

Exon 2 and the surrounding regions were bisulfite sequenced to determine whether other regions of the human INS were also preferentially unmethylated. FIG. 3 depicts a histogram of the tissue methylation pattern of the human INS exon 2 (8CpG), intron 1 (2 CpG) and intron 2 (2 CpG), and the positions of the twelve CpG sites relative to the TSS are indicated in FIG. 3. The bars display the position and percentage of unmethylation (white bars) to methylation (black bars) for each CpG. Each pattern resulted from 5 to 33 clones obtained from 5 individual's blood, 2 individual's beta cells and breast, and 3 individuals for the other tissues. FIG. 3 shows that there were eight CpG sites in exon 2 located at positions +254, +273, +304, +331, +367, +374, +401, and +404 bp relative to the TSS. Two other sites in intron 1 (+127 and +139) and two sites in intron 2 (+456 and +482) were also examined. As in the promoter, these sites were mostly unmethylated in beta cells and methylated in colon, kidney, lung, spleen and stomach (FIG. 3). However, exon 2 was also found to be predominantly unmethylated in blood, breast and liver cells. Therefore, the human INS exon 2 region was not appropriate for targeting beta cell DNA in circulation in the qMSP assay since it did not exhibit a beta cell-specific pattern, especially in blood, the major background signal of the assay.

Example 4: Dose Dependent Amplification of Methyl Specific and Bisulfate-Specific PCR Primer Sets Nested Methylation-Specific PCR (MSP)

Quantitative PCR was performed with a 7500 Real-time PCR instrument (Applied Biosystems, Foster City, Calif.). In First-Step PCR, each reaction contained 20-30 ng of bisulfite-treated DNA, 12.50 QuantiTect SYBR® Green PCR (QIAGEN, Valencia, Calif.) and 500 nM each forward and reverse primer (Table 3) in a total volume of 250. Thermal cycling was initiated with an enzyme activation step of 15 min at 95° C., followed by 15 cycles of 95° C. for 15 s, 60° C. for 30 s, and, 72° C. for 30 s. The PCR products were purified using QIAquick PCR Purification Kit (QIAGEN, Valencia, Calif.). In Second-Step PCR, the products from the first reaction were used as template for a qPCR with nested primers (Table 3). The reactions were initiated with for 15 min at 95° C., followed by 40 cycles of 95° C. for 15 s, 57° C. for 30 s, and, 72° C. for 30 s. The quantification cycle (Cq) was determined for each reaction with methylation-specific primers (MSP) and bisulfite-specific primers (BSP) and the ratio of unmethylated to total amplifiable bisulfite-treated DNA was calculated using the Relative Unmethylation Ratio (RUR) as previously described by Husseiny et al. as Relative Expression Ratio (RER). The second-step reaction Cq values were between 15 and 40. Negative controls without DNA did not yield products in the first-step reaction.

Human Subjects

Human tissues and islet cells were isolated. To enrich beta cells, islets were dissociated with TrypLE (Invitrogen, Carlsbad, Calif.) and stained with Newport Green (Invitrogen, Carlsbad, Calif.) before enriching by fluorescent-activated cell sorting. Normal human tissues such as liver, breast, colon, kidney, lung, spleen, and stomach were obtained from the Pathology Core at City of Hope. Blood samples were collected from normal healthy controls and from patients before and after islet transplantation.

Quantitative Methylation-Specific PCR

The human assay involved six differentially methylated sites. A nested PCR technique was developed and used, which interrogated additional methylation sites while improving both the specificity and sensitivity of the assay. Primers were designed to recognize only unmethylated DNA as found in beta cells (FIG. 4A). Primers P20 and P21 are methylation-specific primers that amplify unmethylated DNA only (FIG. 4A, dashed arrows) targeting CpGs at −357 and −69 and together produce a product of 350 bp (top agarose gel depicted in FIG. 4B). Primers P38 and P39 target CpGs −206 and −135, respectively, and produce a product of 130 bp (bottom agarose gel in FIG. 4B). In addition, two primers, P40 and P41, target the regions just upstream and downstream of P20 and P21, respectively, and were not aligned with any CpG site. P40 and P41 primers are bisulfate-specific primers (BSPs) that amplify both methylated and unmethylated DNA and are shown in FIG. 4A as solid arrows. The P40 and P41 primers amplify a 350 bp product from both methylated and unmethylated DNA (middle agarose gel depicted in FIG. 4B), and therefore provide a measure of total amplifiable insulin gene promoter sequences. These primer sets were evaluated using serial dilutions of the cloned unmethylated insulin gene as a template. As shown, each MSP and BSP primer set exhibited dose dependent amplification ranging from $10^6$ copies to as few as 5 copies of the unmethylated sequences (FIG. 4B).

Example 5: Quantitative Analysis of Bisulfate-Specific (BSP) and qMSP Assays

Statistical Analysis

Statistical significance between samples was tested with a two-tailed Student's t-test for unpaired values or two-way analysis of variance (ANOVA) between human islets and other tissues (colon and blood) using GraphPad Prism 6 software. Statistical significance was defined as a P-value of <0.05, <0.01, and <0.001. Statistical analysis of DNA methylation was done using QUMA (http://quma.cdb.riken.jp/) which performs a Fisher exact test on the methylation status of individual CpG sites using P<0.1, and P<0.01. Data are expressed as mean±SEM.

Qualitative Analysis of Standard Curves of BSP and qMSP Assays

Quantitative analysis of the standard curves shows that the BSP and qMSP assays were linear over a $10^5$-fold range of template concentrations (FIG. 4C). FIG. 4C depicts graph of real time SYBR® Green PCR data showing linearity of Cq versus log copy number of unmethylated plasmid from 5 to $10^6$ copies. For nested PCR, the two MSP assays were applied sequentially, i.e. amplification with P20/P21 followed by P38/P39. Variation across the nested MSP curve ranged from 2.83% to 6.58% (Table 1). Furthermore, the standard curve parameters (Table 2) were highly reproducible for both nested qMSP (efficiency=85.19%±1.37 SD, slope=−3.737±0.05 SD, $R^2$=0.979±0.004 SD; n=5 experiments) and qBSP (efficiency=73.44%±7.81 SD, slope=−4.212±0.32 SD, $R^2$=0.989±0.01 SD; n=5 experiments).

Example 6: Assay Specificity Increases with Increasing CpG Sites Interrogated in the Assay Primers sets (from Example 4, FIG. 4A) were tested for specificity and sensitivity employing serially diluted bisulfite converted gDNA from human islets, blood, and colon as templates for qMSP. Fold changes in unmethylation were calculated by the Relative Unmethylation Ratio (RUR) for each sample (See FIG. 1C for RUR description) in which the level of beta cell DNA (qMSP) was normalized for total amplifiable sequences (qBSP). To assess the effect of targeting 2 versus 4 CpG sites, the nested reaction using P38/P39 was preceded by a first reaction using either BSP primers (P40/P41) to target a total of 2 sites or MSP primers (P20/P21) to target 4 sites. The assay interrogating 2 CpG sites exhibited a highly significant specificity for islets over blood and colon (FIG. 5A). However, the assay targeting 4 sites showed a greater difference in signal between islets and other tissues, indicating that the specificity of the assay was increased by increasing the number of CpG sites interrogated in the assay (FIG. 5B).

Figure 6A:
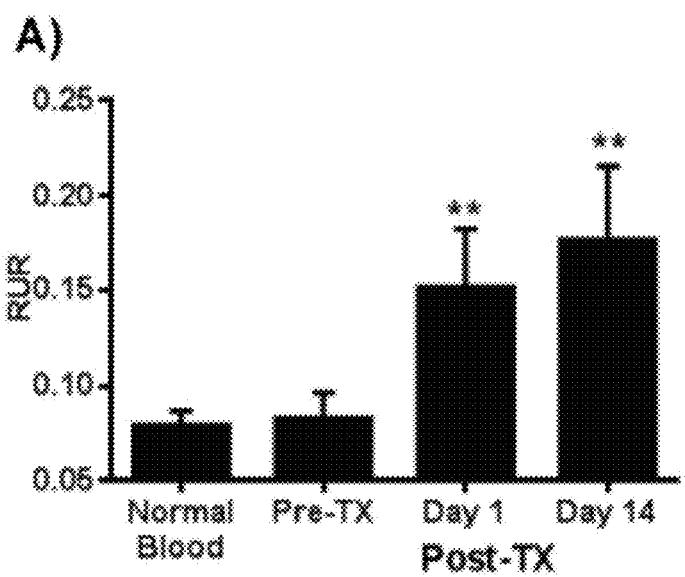
FIGS. 6A-6B show histograms of quantitative MSP for monitoring beta cells in islet transplant patients.
Figure 6B:
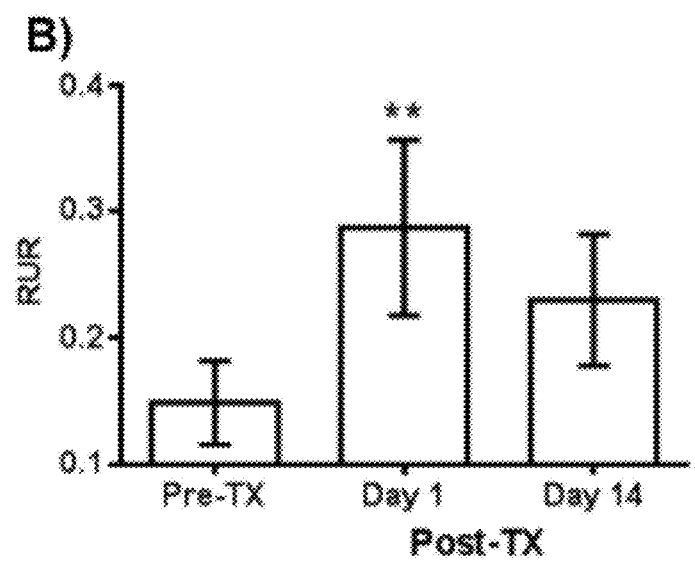

Example 7: Quantitative MSP for Monitoring Circulating Beta Cell DNA in Islet Transplant Patients The application of the qMSP assay to human studies was assessed using blood samples from clinical islet transplant patients. Samples were obtained from islet recipients (n=6) prior to transplantation (TX) and on post-transplant days 1 and 14. These were compared with blood (FIG. 6A) from healthy donors (n=6) using the qMSP assay. Plasma fractions (FIG. 6B) were also prepared and compared with the results of whole blood to determine whether plasma was a better starting point for the assay. Prior to transplantation, there was no significant difference in the qMSP signal between the patient samples and normal controls (FIG. 6A; Mann-Whitney U test; p=0.92). However, the qMSP signal rose significantly the day after islet transplantation (Wilcoxon test; p=0.005) and remained elevated for at least fourteen days (Wilcoxon test; p=0.004) in the whole blood samples (FIG. 6A). In plasma samples, the signal also rose significantly on day 1 (FIG. 6B; Wilcoxon test; p=0.003), though in contrast to whole blood, fell again by day 14 (Wilcoxon test; p=0.58). Beta cell DNA is associated with cells in the blood and prolongs the qMSP signal. qMSP can be used herein to monitor beta cell DNA in human clinical samples and the duration of the signal is longer in whole blood than in plasma.

Example 8: MSP Assay and Mixed Meal Tolerance Test on New Onset T1D Patients Patient Characterization Patients in the study were newly diagnosed T1D patients, 12 years or older, healthy individuals with no cancer and not pregnant. Patients were also willing to comply with the scheduled visits to the clinic under the continuing care of their endocrinologists. The patients were diagnosed on American Diabetic Association (ADA) criteria of elevated blood glucose and, HbA1c, as well as the presence of one or more positive antibody titers.

Study Design and Methods

Fasting blood samples were drawn at time of diagnosis, 2 weeks, 1, 2, 4, 6, 9, and 12 months. Blood samples were analyzed with fasting blood glucose levels, fasting serum c-peptide, HbA1c, serum auto-antibody tiers and MSP assays. To evaluate residual islet mass, stimulated c-peptide level following a mixed-meal tolerance test (MMTT) at baseline and at 3 month intervals was measured. The longitudinal relationship between the metabolic parameters and the appearance of beta cell DNA in circulation was analyzed by MSP.

TABLE 5

| | | | | | | |
|---|---|---|---|---|---|---|
| | | | Patient Characteristics* | | | |
| # | Gender (M/F) | GAD65 Ab (nmol/L) (≤0.02) | Insulin Ab (nmol/L) (0.0-0.02) | Islet Antigen 2 (IA-2) (nmol/L) (≤0.02) | HbA1C (4.8%-5.9%) | Age/Yr |
| 1 | M | 0.01 | 0.01 | 11.5 | 12.70% | 15 |
| 2 | F | 0 | 0 | 3.23 | 18.50% | 14.3 |
| 3 | M | 0.18 | 0 | 0 | 12.90% | 16.5 |
| 4 | M | 0.17 | 0 | 2.99 | 9.10% | 14.7 |
| 5 | M | 5.91 | 0 | 1.97 | 11.60% | 12.8 |
| 6 | M | 0.06 | 0 | 0.14 | 12.80% | 14.3 |
| 7 | M | 0.08 | 0 | 2.42 | 13.00% | 13.3 |
| 8 | M | n/d | n/d | n/d | 7.80% | 14.5 |
| 9 | M | 1.21 | 0 | 0.03 | 7.40% | 14.5 |
| 10 | F | 0 | 0 | 0 | 12.20% | n/d |

*60% are positive for GAD65 Ab, 70% are positive for IA-2 Ab, 50% are positive for GAD65 and IA-2b Abs.

Figure 7A:
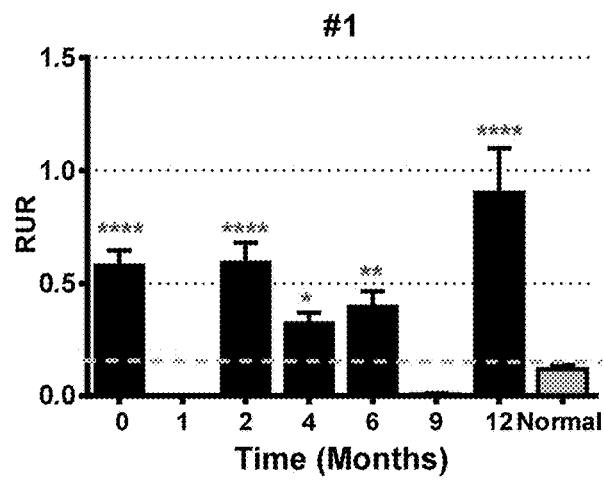
FIGS. 7A-7AA show histograms of MSP assay and Mixed Meal Tolerance Test (MMTT) of patients.
Figure 7B:
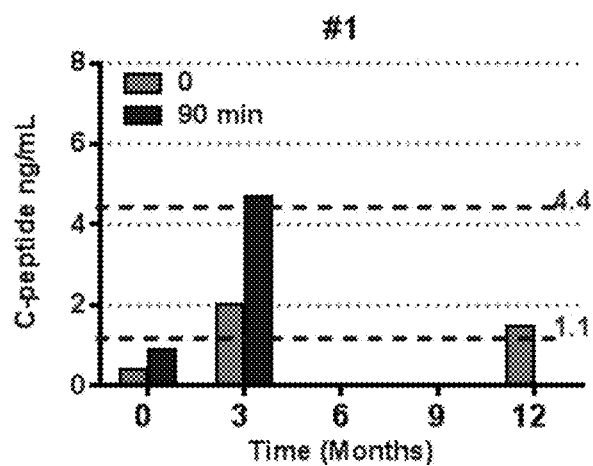
Figure 7C:
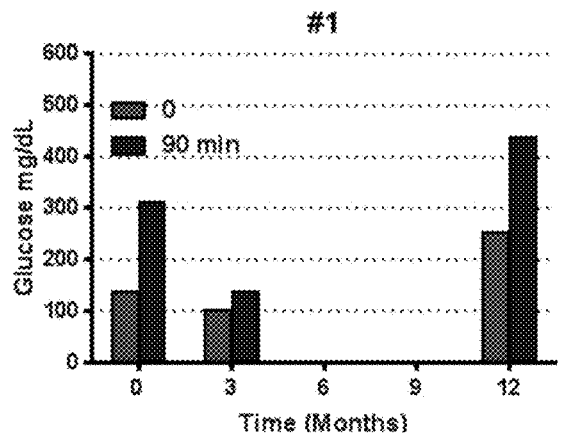

Patients were monitored with new onset of T1D age 12 years and older starting within the first 3 months of diagnosis. Evaluations were made throughout the first year post-diagnosis, focusing on evidence of beta cell loss as well as glycemic control. All T1D patients were diagnosed based on ADA criteria of elevated blood glucose and, HbA1c, as well as the presence of one or more positive autoantibody titers (insulin, GAD65 and IA-2 antibodies). Blood samples were collected at diagnosis, 1, 2, 4, 6, 9 and 12 months post-diagnosis and analyzed by MSP assay (FIGS. 7A-7AA). Results indicated that 60% and 70% of patients were positive for GAD65 and IA-2 autoantibodies, respectively. HbA1c ranged between 9.1% and 18.5% at diagnosis and subsequently decreased after initiation of insulin therapy. Stimulated C-peptide levels at diagnosis were very low, but increased with meal stimulation once the patient started insulin therapy, but declined again over time (FIGS. 7A-7AA, middle histogram of each patient). At diagnosis, high insulin amounts were required and decreased once the patient started insulin therapy. Most of the patients showed high signal of C-peptide after stimulation. Using the MSP assay, a significantly increased relative unmethylation ratio (RUR) of insulin DNA that is compatible with the known timeline of beta cell death in early onset T1D was observed (FIGS. 7A-7AA, left histogram of each patient).

Example 9

A system for detecting unmethylated DNA is provided in this example. FIG. 8 shows a system diagram illustrating a system 800 for detecting unmethylated DNA in a subject, in accordance with some example embodiments. Referring to FIG. 8, in some example embodiments, the system 800 is realized in digital electronic circuitry, integrated circuitry, specially designed application specific integrated circuits (ASICs), field programmable gate arrays (FPGAs) computer hardware, firmware, software, and/or combinations thereof. The system 800 is configured to communicate with one or more devices (e.g., personal computers, workstations, tablet personal computers, and/or smartphones) via a wired and/or wireless network 820. For example, as shown, the system 800 communicates with a device 830.

In some example embodiments, the system 800 includes one or more processor to implement a plurality of modules including, but not limited to, a DNA data collection module 210, a detection module 212, a diagnostic module 214, a treatment module 216, and a user interface module 218. The system 800 includes additional and/or different modules without departing from the scope of the present disclosure.

The DNA data collection module 210 is configured to collect DNA data. In some example embodiments, the DNA data collection module 210 collects DNA data that has been generated by isolating DNA from a sample (e.g., fluid, tissue) of a subject. To generate the DNA data, the isolated DNA is further subject to modification and/or amplification. For example, modifying the isolated DNA includes modifying unmethylated cytosine in the DNA to produce DNA that includes uridine. Thereafter, the DNA including uridine is amplified through polymerase chain reaction (PCR) (e.g., qMSP) with methylation specific primers.

According to some example embodiments, the DNA data includes sequencing data that corresponds to the amplified DNA. As such, in some embodiments, the DNA data collection module 210 is communicatively coupled to a DNA sequencer (not shown) adapted to automate the sequencing of DNA that has been isolated, modified, and amplified as discussed above. In addition, in some example embodiments, the DNA data collection module 210 is communicatively coupled with one or more DNA processing apparatuses (not shown) via the network 820. For example, the DNA data collection module 210 is coupled with one or more apparatuses adapted to automate the performance DNA isolation (e.g., robotic fluid handling systems), modification, and amplification (e.g., thermal cycler).

The detection module 812 is configured to detect unmethylated DNA based on DNA data (e.g., collected by the DNA data collection module 810). For example, in some example embodiments, the detection module 812 is configured to detect unmethylated promoter DNA at a CpG site of the insulin gene. The detection of unmethylated insulin gene promoter is used as a measure of beta cell death and a prognostic indicator for autoimmunity resulting in T1D.

The diagnostic module 814 is configured to provide a diagnosis and/or prognosis for a subject based on results from the detection module 812. In example embodiments, based on the unmethylated DNA detected in a subject, the diagnostic module 814 provides a prognosis of whether the subject is at risk for developing T1D. For example, the diagnostic module 814 performs statistical analysis (e.g., using QUMA and Fisher exact test) on the detected unmethylated DNA to generate a prognosis for a subject.

Alternatively or additionally, based on the detected unmethylated DNA in the subject, the diagnostic module 814 also is able to provide a diagnosis of the presence of actual ongoing T1D in the subject. The diagnostic module 814 is able to provide a diagnosis of the presence of actual ongoing T1D before the subject exhibits any loss of metabolic control.

The treatment module 816 is configured to devise a treatment plan for a subject based on results from the diagnostic module 814. In some example embodiments, the treatment module 816 determines, based on a subject's diagnosis and/or prognosis, a treatment plan that includes, but is not limited to, preventative care, medication, and/or islet cell transplantation.

The user interface module 818 is configured to generate a user interface through which a user (e.g., a physician) interacts with the system 800. For example, the user interface module 818 provides one or more user interfaces configured to provide a prognosis and/or diagnosis from the diagnostic module 814 and/or a treatment plan from the treatment module 816. The user interfaces are graphic user interfaces (GUIs) adapted to provide visual outputs to and/or receive inputs from the user.

FIG. 9 shows a flowchart illustrating a process 900 for detecting unmethylated DNA in a subject, in accordance with some example embodiments. Referring to FIGS. 8-9, the process 900 is performed by the system 800.

At 902, the system 800 (e.g., the DNA data collection module 810) collects DNA data associated with a subject. For example, in some example embodiments, the system 800 (e.g., the DNA data collection module 810) collects DNA data that has been generated by isolating a subject's DNA from a sample (e.g., fluid, tissue). The isolated DNA is further modified and/or amplified. According to some example embodiments, the DNA data is sequencing data (e.g., from a DNA sequencer) that corresponds to the amplified DNA.

At 904, the system 800 (e.g., the detection module 812) detects unmethylated DNA at a CpG site in an insulin gene promoter based on the DNA data. In some example embodiments, the detection of unmethylated insulin gene promoter is used as a measure of beta cell death and a prognostic indicator for autoimmunity resulting in T1D.

At 906, the system 800 (e.g., the diagnostic module 814) provides a prognosis and/or a diagnosis for the subject based on detected unmethylated DNA. In some example embodiments, based on unmethylated DNA detected in a subject, the system 800 provides a prognosis of the subject's risk for developing T1D and/or a diagnosis of actual ongoing T1D (e.g., before subject exhibits loss of metabolic control).

At 908, the system 800 (e.g., the treatment module 816) provides a treatment plan based on the prognosis and/or diagnosis. For example, in some example embodiments, the system 800 determines a treatment plan that includes, but is not limited to preventative care, medication, and/or islet cell transplantation.

The process 900 can include additional and/or different operations without departing from the scope of the present disclosure. One or more operations of the process 900 is omitted and/or repeated without departing from the scope of the present disclosure.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims

What is claimed is:

1. A method of detecting unmethylated deoxyribonucleic acid (DNA) in a subject, the method comprising isolating DNA from a blood sample of said subject; contacting said isolated DNA with bisulfite for modifying unmethylated cytosine at a CpG site in said DNA to uridine; and detecting unmethylation of said CpG site in an insulin gene promoter located at −19 bp, −69 bp, −135 bp, −206 bp, or −357 bp relative to the transcription start site.

2. The method of claim 1, wherein said detecting comprises: amplifying said DNA comprising uridine using quantitative methylation-specific polymerase chain reaction (qMSP) with methylation specific primers; thereby detecting unmethylation at said CpG site.

3. The method of claim 1 or 2, wherein said DNA is from beta cells of said subject.

4. The method of claim 3, wherein said beta cells are undergoing cell death.

5. The method of claim 4, wherein said beta cells are undergoing programmed cell-death.

6. The method of claim 4, wherein said beta cells are undergoing non-programmed cell death.

7. The method of claim 4, wherein said beta cells are undergoing death due to an autoimmune response.

8. The method of claim 2, wherein said methylation specific primer hybridizes to said CpG site.

9. The method of claim 8, wherein said methylation specific primer comprises SEQ ID NO: 1, 2, 3, or 4.

10. The method of claim 8, wherein said detecting unmethylation at said CpG site comprises detecting unmethylation at two or more said CpG sites on said insulin gene promoter.

11. The method of claim 2, wherein said subject is a human with a family history of type I diabetes (T1D).

12. The method of claim 1, wherein said blood sample is whole blood, plasma, or serum of said subject.

13. A method of treating autoimmunity against beta cells in a subject having unmethylated CpG at −19 bp, −69 bp, −135 bp, −206 bp, or −357 bp relative to the transcription start site of an insulin gene promoter of beta cells, determined by the method as set forth in claim 2, comprising administering to said subject an agent for treating T1D, thereby treating T1D of said subject.

14. The method of claim 13, wherein the autoimmunity results in T1D.

15. The method of claim 13, wherein the agent is insulin.

16. The method of claim 15, wherein the insulin is administered by injection or an insulin pump.

17. The method of claim 13, wherein the agent is cyclosporine, anti-CD3 antibody, or anti-CD20 antibody.

18. The method of claim 13, wherein the agent is a cytokine selected from the group consisting of: human growth hormone, N-methionyl human growth hormone, and bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, fibroblast growth factor, prolactin, placental lactogen, tumor necrosis factor α and/or β, mullerian-inhibiting substance, mouse gonadotropin-associated peptide, inhibin, activing, vascular endothelial growth factor, integrin, thrombopoietin (TPO), nerve growth factors such as NGF-β, platelet-growth factor, transforming growth factors (TGFs) TGF-α and/or TGF-β, insulin-like growth factor-I and/or -II, erythropoietin (EPO), osteoinductive factors; interferons such as interferon-α, β, and γ; colony stimulating factors (CSFs) such as macrophage-CSF (M-CSF), granulocyte-macrophage-CSF (GM-CSF), and granulocyte-CSF (G-CSF), interleukins (ILs) IL-1, IL-1α, IL-2, IL-3, IL-4, IL-5, IL-6, IL-7, IL-8, IL-9, IL-11, IL-12, IL-13, IL-16, IL-17, IL-18, IL-22, IL-23, IL-27, IL-35, and/or IL-35; tumor necrosis factor TNF-α and/or TNF-β; and kit ligand (KL).

19. The method of claim 13, wherein the agent is for immunotherapy to ameliorate autoimmunity against beta cells, and symptoms thereof.

20. The method of claim 13, further comprising transplanting pancreas or islet cells to said subject.

21. A system, comprising:
at least one processor; and
at least one memory including program code which when executed by the one memory provides operations comprising:
collecting deoxyribonucleic acid (DNA) data associated with a subject;
contacting isolated DNA from a blood sample of a subject with bisulfite for modifying unmethylated cyctosine at a CpG site in said DNA to uridine detecting unmethylation of DNA at said CpG site in an insulin gene promoter located at −19 bp, −69 bp, −135 bp, −206 bp, or −357 bp relative to the transcription start site; and providing, via a user interface, a prognosis and/or diagnosis for the subject based at least in part on detected unmethylated DNA.

22. The system of claim 21, further configured to provide, via the user interface, a treatment plan determined based at least in part on the prognosis and/or diagnosis.

23. The system of claim 21, wherein the detecting of unmethylation at the CpG site comprises detecting unmethylation at two or more CpG sites on the insulin gene promoter.

24. The system of claim 21, wherein the subject comprises a human having a family history of a type of diabetes.

25. The system of claim 21, wherein the blood sample comprises whole blood, plasma, or serum.

26. The system of claim 21, wherein the DNA data comprises sequencing data corresponding to DNA isolated from a blood sample of the subject.

27. The system of claim 26, wherein the isolated DNA is modified by at least modifying unmethylated cystosine in the isolated DNA to produce DNA that includes uridine.

28. The system of claim 27, wherein the DNA that includes uridine is amplified by quantitative methylation-specific polymerase chain reaction (qMSP) with methylation specific primers.

29. The system of claim 28, wherein the methylation specific primer hybridizes to the CpG site.

30. The system of claim 28, wherein the methylation specific primer comprises SEQ ID NO: 1, 2, 3, or 4.

31. The system of claim 26, wherein the DNA comprises DNA from beta cells of the subject.

32. The system of claim 31, wherein the beta cells comprise cells undergoing programmed or non-programmed cell-death as a result of an autoimmune response.

* * * * *

SEQUENCE LISTING

```
<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 1 atagggtgt ggggataggg gtttggggat agtagt                                    36

<210> SEQ ID NO 2
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 2 aaccatctc ccctacctct caaccctac ca                                         32

<210> SEQ ID NO 3
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 3
```

```
tgggtttttg gttaagattt taatgattt                                29
```

<210> SEQ ID NO 4
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 4

```
caacaaataa ctaaaaacta aaactacaat ttcca                         35
```

<210> SEQ ID NO 5
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 5

```
ataggggtgt ggggataggg gtttggggat agta                          34
```

<210> SEQ ID NO 6
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 6

```
caaaacccat ctcccctacc tctcaacccc tac                           33
```

<210> SEQ ID NO 7
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 7

```
ggtttaggat tttagggtgg tt                                       22
```

<210> SEQ ID NO 8
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 8

```
cccccttcta cccatactaa at                                       22
```

<210> SEQ ID NO 9
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 9

```
tgtggggata ggggtttggg gatagta                                  27
```

<210> SEQ ID NO 10
<211> LENGTH: 40
<212> TYPE: DNA

```
<213> ORGANISM: Artificial Sequence
<220> FEATURE:
<223> OTHER INFORMATION: Synthetic polynucleotide

<400> SEQUENCE: 10
cctcttctaa tacaacctat cctaaaaaac taaaaactac                          40

<210> SEQ ID NO 11
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 11
tgtggggaca ggggtctggg gaca                                          24

<210> SEQ ID NO 12
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 12
agcctcctgc cccttctgc ccat                                           24

<210> SEQ ID NO 13
<211> LENGTH: 1960
<212> TYPE: DNA
<213> ORGANISM: Homo sapiens

<400> SEQUENCE: 13
ggggacaggg gtgtggggac aggggtgtgg ggacaggggt gtggggacag gggtctgggg    60 acagggtgt ggggacaggg gtcctgggga caggggtgtg gggatagggg tgtggggaca   120
ggggtgtggg gacaggggtg tggggacagg ggtctgggga cagcagcgca aagagccccg   180
ccctgcagcc tccagctctc tggtctaatg tggaaagtg gcccaggtga gggctttgct    240
ctcctggaga catttgcccc cagctgtgag caggacagg tctggccacc gggcccctgg    300
ttaagactct aatgacccgc tggtcctgag gaagaggtgc tgacgaccaa ggagatcttc    360
ccacagaccc agcaccaggg aaatggtccg gaaattgcag cctcagcccc agccatctg    420 ccgaccccc caccccaggc cctaatgggc caggcggcag gggttgagag gtaggggaga   480
tgggctctga gactataaag ccagcggggg cccagcagcc ctcagccctc caggacaggc   540
tgcatcagaa gaggccatca agcaggtctg ttccaagggc ctttgcgtca ggtgggctca   600
ggattccagg gtggctggac cccaggcccc agctctgcag cagggaggac gtggctgggc   660
tcgtgaagca tgtggggtg agcccagggg ccccaaggca gggcacctgg ccttcagcct    720
gcctcagccc tgcctgtctc ccagatcact gtccttctgc catggccctg tggatgcgcc    780 tcctgccct gctggcgctg ctggcccctct ggggacctga cccagccgca gcctttgtga    840
accaacacct gtgcggctca cacctggtgg aagctctcta cctagtgtgc gggaacgag     900 gcttcttcta cacacccaag acccgccggg aggcagagga cctgcagggt gagccaactg    960
cccattgctg cccctggccg cccccagcca cccctgctc ctggcgctcc cacccagcat   1020 ggcagaagg gggcaggagg ctgccaccca gcaggggtc aggtgcactt ttttaaaaag    1080
aagttctctt ggtcacgtcc taaaagtgac cagctccctg tgcccagtc agaatctcag   1140 cctgaggacg tgttggctt cggcagcccc gagatacatc agagggtggg cacgctcctc    1200
```

```
cctccactcg cccctcaaac aaatgccccg cagcccattt ctccaccctc atttgatgac    1260
cgcagattca agtgttttgt taagtaaagt cctgggtgac ctggggtcac agggtgcccc    1320
acgctgcctg cctctgggcg aacaccccat cacgcccgga ggagggcgtg gctgcctgcc    1380
tgagtgggcc agaccctgt cgccaggcct cacggcagct ccatagtcag agatggggga     1440
agatgctggg gacaggccct ggggagaagt actgggatca cctgttcagg ctcccactgt    1500
gacgctgccc cggggcgggg gaaggaggtg ggacatgtgg gcgttggggc ctgtaggtcc    1560
acacccagtg tgggtgaccc tccctctaac ctgggtccag cccggctgga gatgggtggg    1620
agtgcgacct agggctggcg ggcaggcggg cactgtgtct ccctgactgt gtcctcctgt    1680
gtccctctgc ctcgccgctg ttccggaacc tgctctgcgc ggcacgtcct ggcagtgggg    1740
caggtggagc tgggcggggg ccctggtgca ggcagcctgc agcccttggc cctggagggg    1800
tccctgcaga agcgtggcat tgtggaacaa tgctgtacca gcatctgctc cctctaccag    1860
ctggagaact actgcaacta gacgcagccc gcaggcagcc ccacacccgc cgcctcctgc    1920
accgagagag atggaataaa gcccttgaac cagccctgct                          1960

<210> SEQ ID NO 14
<211> LENGTH: 435
<212> TYPE: DNA
<213> ORGANISM: Homo sapiens

<400> SEQUENCE: 14
gacaggggtg tggggatagg ggtgtgggga caggggtgtg gggacagggg tgtggggaca      60
ggggtctggg gacagcagcg caaagagccc cgccctgcag cctccagctc tcctggtcta    120
atgtggaaag tggcccaggt gagggctttg ctctcctgga gacatttgcc ccagctgtg    180 agcagggaca ggtctggcca ccgggcccct ggttaagact ctaatgaccc gctggtcctg    240
aggaagaggt gctgacgacc aaggagatct tcccacagac ccagcaccag ggaaatggtc    300
cggaaattgc agcctcagcc cccagccatc tgccgacccc ccacccag gccctaatgg     360 gccaggcggc aggggttgag aggtagggga gatgggctct gagactataa agccagcggg    420
ggcccagcag ccctc                                                     435

<210> SEQ ID NO 15
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 15
gtggggatag ggtgtggggg ataggggtgt ggggatagg gtgtggggat aggggtttgg     60
ggatagtagt gtaaagagtt ttgttttgta gtttttagtt tttttggttt aatgtggaaa    120
gtggtttagg tgagggtttt gttttttttgg agatatttgt tttagttgt gagtagggat    180 aggtttggtt attgggtttt tggttaagat tttaatgatt tgttggtttt gaggaagagg    240
tgttgatgat taaggagatt ttttatagat tttagtatta gggaaatggt ttggaaattg    300
tagttttagt ttttagttat ttgttgattt ttttatttta ggttttaatg ggttaggtgg    360
taggggttga gaggtagggg agatgggttt tgagattata agttagtgg gggtttagta    420 gtttttt                                                              426

<210> SEQ ID NO 16
```

```
<211> LENGTH: 426
<212> TYPE: DNA
<213> ORGANISM: Artificial Sequence
<220> FEATURE:
<223> OTHER INFORMATION: Synthetic polynucleotide

<400> SEQUENCE: 16
gtggggatag gggtgtgggg atagggtgt ggggataggg gtgtggggat aggggtttgg    60
ggatagtagc gtaaagagtt tcgtttttgta gttttttagtt tttttggttt aatgtggaaa   120
gtggtttagg tgagggtttt gttttttttgg agatatttgt tttagttgt gagtagggat    180 aggtttggtt atcgggtttt tggttaagat tttaatgatt cgttggtttt gaggaagagg    240
tgttgacgat taaggagatt tttttataga tttagtatta gggaaatggt tcggaaattg    300 tagtttagt ttttagttat ttgtcgattt ttttatttta ggttttaatg ggttaggcgg    360
taggggttga gaggtagggg agatgggttt tgagattata aagttagcgg gggtttagta    420
gttttt                                                                426
```